United States Patent [19]
Jacobsen et al.

[11] Patent Number: 5,663,393
[45] Date of Patent: Sep. 2, 1997

[54] CHIRAL CATALYSTS AND EPOXIDATION REACTIONS

[75] Inventors: Eric N. Jacobsen, Mohamet, Ill.; Wei Zhang, Maple Glen, Pa.; Li Deng, Urbana, Ill.

[73] Assignee: Research Corporation Technologies, Inc., Tucson, Ariz.

[21] Appl. No.: 465,963

[22] Filed: Jun. 6, 1995

Related U.S. Application Data

[63] Continuation of Ser. No. 938,245, Oct. 15, 1992, and PCT/US92/07261 Aug. 26, 1992, published as WO93/03838 Mar. 4, 1993, which is a continuation-in-part of Ser. No. 809,446, Dec. 16, 1991, abandoned, which is a continuation-in-part of Ser. No. 749,460, Aug. 26, 1991, abandoned, and a continuation-in-part of Ser. No. 673,208, Mar. 21, 1991, abandoned, which is a continuation-in-part of Ser. No. 496,992, Mar. 21, 1990, abandoned.

[51] Int. Cl.$^6$ .............. C07F 13/00; C07F 9/00; C07F 7/00; C07F 15/00
[52] U.S. Cl. .............. 556/45; 502/167; 549/337; 549/510; 549/524; 549/525; 549/531; 549/533; 556/32; 556/34; 556/42; 556/56; 556/57; 556/150; 556/137; 568/27
[58] Field of Search ................ 556/32, 34, 42, 556/45, 56, 57, 150, 137; 549/525, 524, 531, 533, 337, 510; 568/27; 502/167

[56] References Cited

U.S. PATENT DOCUMENTS 4,924,011  5/1990  Denis et al. .............. 549/510

OTHER PUBLICATIONS

Akbulut, et al., "The Triplex Diels–Alder Reaction of 1,3-Dienes with Enol, Alkene, and Acetylenic Dienophiles: Scope and Utility," *J. Org. Chem.*, vol. 54, No. 11, 1989, pp. 2549–2556.

Banfi, et al., "Investigation on Factors Ruling Catalytic Efficiency and Chemical Stability of Mn(III) Porphyrins in HOCl Olefin Epoxidation; Conditions for Practical Application," *J. Org. Chem.*, vol. 54, No. 8, 1989.

Bergmann, et al., "4–Heterocyclyloxy–2H–1–benzopyran Potassium Channel Activators," *J. of Medicinal Chem.*, 1990, vol. 33, No. 10, pp. 2759–2767.

Borman, *Chem. & Eng. News*, Sep. 2, 1991, pp. 11–18.

Boucher, *J. Inorg. Nucl. Chem.*, vol. 36, p. 531 (1974).

Casiraghi, et al., "Selective Reactions Between Phenols and Formaldehyde. A Novel Route to Salicylaldehydes", *J.C.S. Perkin I*, 1980, pp. 1862–1865.

Cesarotti, et al., "Optically Active Complexes of Schiff Bases. Part 6.$^1$ Palladium(II) and Platinum(II) Complexes with Quadridentate Schiff Bases of Salicylaldehyde", *J.C.S. Dalton*, 1981, pp. 2147–2152.

Che, et al., "Manganese(III) Amide Complexes as a New Class of Catalyst for Efficient Alkene Epoxidation", *J. Chem. Soc., Chem. Commun.*, 1986, pp. 1443–1444.

Coleman et al., "Characterization and Electrochemistry of Manganese(III) Complexes Containing Pentadentate Ligands," *Inorg. Chem.* vol. 20, No. 4, 1253–1258 (1981).

Collins, et al. "A Water–Stable Manganese(V)–Oxo Complex: Definitive Assignment of a Infrared Vibration," *J. Am. Chem. Soc.*, vol. 112, No. 2, 899–901, (1990).

Collins, et al., "A Manganese (V)–Oxo Complex," *J. Am. Chem. Soc.*, vol. 111, No. 12, 4511–4513, (1989).

Colombo, et al., "Chiral Induction in the Oxidation of Thioanisole with Chiral Oxotitanium(IV) Schiff Bases Complexes as Catalysts. The Importance of the Conformation of the Ligands", *Gazz. Chim. Ital.*, pp. 35–40, (1986).

Corey, et al. "Practical Enantioselective Diels–Alder and Aldol Reactions Using a New Chiral Controller System," *J. Am. Chem. Soc.*, vol. 111, No. 14, pp. 5493–5495, (1989).

Curci, et al., "Asymmetric Epoxidation of Unfunctionalized Alkenes by Dioxirane Intermediates Generated from Potassium Peroxomonosulphate and Chiral Ketones", *J. Chem. Soc., Chem. Commun.*, pp. 155–156, (1984).

Davis, "Chemistry of Oxaziridines. 4.$^1$ Asymmetric Epoxidation of Unfunctionalized Alkenes Using Chiral 2–Sulfonyloxaziridines: Evidence for a Planar Transition State Geometry", *J. Am. Chem. Soc.*, vol. 105, pp. 3123–3128, (1983).

Davis, et al., "Asymmetric Epoxidation of Nonfunctionalized Alkenes with High Enantioselectivity Using Chiral Sulfamyloxaziridines", *Tetrahedron Letters*, vol. 27 No. 42, pp. 5079–5082, (1986).

(List continued on next page.)

*Primary Examiner*—Porfirio Nazario-Gonzalez
*Attorney, Agent, or Firm*—Brinks Hofer Gilson & Lione

[57] ABSTRACT

Chiral catalysts for enantioselectively epoxidizing a prochiral olefin and for enantioselectively oxidizing a prochiral sulfide are disclosed, together with methods of using such catalysts. In accordance with one aspect of the invention, the catalyst is a salen derivative which has the following general structure:

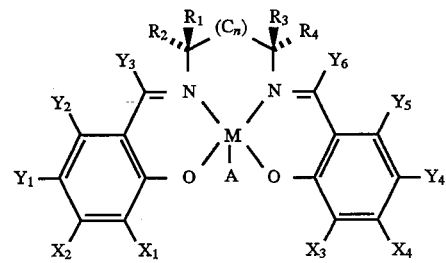

In accordance with another aspect of the present invention is a method of producing an epoxychroman using a chiral catalyst. In accordance with this method, a chromene derivative, an oxygen atom source, and a chiral catalyst are reacted under such conditions and for such time as is needed to epoxidize said chromene derivative. In accordance with yet another aspect of this invention is a method of enantioselectively epoxidizing a cis-cinnamate derivative to make taxol or an analog thereof. In accordance with another aspect a method of disproportionation of hydrogen peroxide using the catalysts of the present invention is disclosed.

81 Claims, 10 Drawing Sheets

OTHER PUBLICATIONS

Denis et al., "A Highly Efficient, Practical Approach to Natural Taxol", *J. Am. Chem. Soc.*, vol. 110, No. 17, pp. 5917–5919, (1988).

Fourneron, et al., "Microbial Transformations. 12. Regiospecific and Asymmetric Oxidation of the Remote Double Bond of Geraniol," *J. Org. Chem.*, vol. 54, No. 19, pp. 4686–4689, (1989).

Ganeshpure et al., "Epoxidation of Alkenes with Iodosylbenzene Catalysed by a Water–Soluble Chromium (III) N,N–Ethylene bis(salicylideneaminato)(salen) Complex Using B–Cyclodextrin as a Phase Transfer Agent," *J. Chem. Soc. Chem. Commun.*, 1988, pp. 981–982.

Gao, et al., "Catalytic Asymmetric Epoxidation and Kinetic Resolution: Modified Procedures Including in Situ Derivatization", *J. Am. Chem. Soc.*, vol. 109, No. 19, pp. 5765–5780, (1987).

Goto et al., "Analysis of the Induction Period and Proposal of Mechanism of the Catalyst of 3–Methylindole Oxygenation by Two Isomers of N,N'–(1,2–Cyclohexylene) bis (3–tert–butylsalicylideneaminato) cobalt (II)", *Chem. Pharm. Bull.*, 33(6), pp. 2195–2203 (1985).

Groves, et al., "Catalytic Asymmetric Epoxidations with Chiral Iron Porphyrins", *J. Am. Chem. Soc.*, vol. 105, No. 18, pp. 5791–5796, (1983).

Groves, et al., "Asymmetric Hydroxylation, Epoxidation, and Sulfoxidation Catalyzed by Vaulted Binaphthyl Metalloporphyrins," *J. Org. Chem.*, vol. 55, No. 11, 3628–3634, (1990).

Halterman et al., "Catalytic Asymmetric Epoxidation of Unfunctionalized Alkenes Using the First $D_4$–Symmetric Metallotetraphenylporphyrin", *J. Org. Chem.*, 56:5253 (1991).

Hassine, et al., "Utilisation de la Synthese Atrolactique Pour L'Evaluation de L'Evaluation de L'Efficacite D'Inducteurs de Synthese Asymetrique", *Bull. Soc. Chim. Belg.*, vol. 95, pp. 547–566, (1986).

Helder, et al., "Catalytic Asymmetric Induction in Oxidation Reactions", *Tetra. Lett.*, No. 21, pp. 1831–1834, (1976).

Hopkins, et al., "Iron(III) Complexes of Chiral Bipyridine Macrocycles as Novel Metallocatalysts", *J. Chem. Soc., Chem. Commun.*, 1987, pp. 171–173.

Hosoya, et al., "Enantioselective Epoxidation of Olefins with Chiral (Salen) Manganese (III) Complexes Bearing 4–Methyl–3–[R)–1phenylpropyl]salicylideneamine as a Constituent", *Synlett*, Sep. 1991, pp. 691–692.

Irie, et al., "Enantioselective Epoxidation of Unfunctionalized Olefins Using Chiral (Salen) Manganese (III) Complexes," *Tetra. Lett.*, vol. 32, No. 8, pp. 1055–1058, 1991.

Irie, et al., "Catalytic Epoxidation with Molecular Oxygen Using Nickel Complex," *Tetra. Lett.*, vol. 32, No. 47, pp. 6891–6894, 1991.

Irie et al., "Donor Ligand Effect in Asymmetric Epoxidation of Unfunctionalized Olefins with Chiral Salen Complexes," *Synlett*, Apr. 1991, pp. 265–266.

Irie, et al., "Catalytic Asymmetric Epoxidation of Unfunctionalized Olefins", Using Chiral (Salen) manganese (III) Complexes, *Tetra.*, vol. 2, No. 7, pp. 481–494, 1991.

Irie, et al., "Catalytic Asymmetric Epoxidation of Unfunctionalized Olefins," *Tetra. Lett.*, vol. 31, No. 50, pp. 7345–7348, 1990.

Jacobsen et al., "Electronic Tuning of Asymmetric Catalysts," *J. Am. Chem. Soc.*, vol. 113, No. 17, 1991.

Jacobsen, et al., "Asymmetric Dihydroxylation via Ligand–Accelerated Catalysis," *J. Am. Chem. Soc.*, vol. 110, No. 6, pp. 1968–1970, (1988).

Jacobsen et al., "Highly Enantioselective Epoxidation Catalysts Derived from 1,2–Diaminocyclohexane," *J. Am. Chem. Soc.*, vol. 113, No. 18, pp. 7063–7064, (1991).

Kagan, et al., "Asymmetric Epoxidation of Simple Olefins with an Optically Active Molybdenum (VI) Peroxo Complex", *Angew. Chem. Int. Ed. Engl.* vol. 18, No. 6, pp. 485–486, (1979).

Kanatomi et al., "The Dehydrogenation of Nickel(II) Chelates of rac–and meso–2,2'–[1,2,–Diphenylethylene)bis(iminomethylene)]diphenol and Related Compounds," *Chem. Soc. of Japan Bull.*, vol. 56, No. 1, pp. 99–104, (1983).

Katsuki, T. "The First Practical Method for Asymmetric Epoxidation", *J. Am. Chem. Soc.*, vol. 102, No. 18, pp. 5974–5976, (1980).

Kinneary, et al., "Alkene Epoxidation Using Ni(II) Complexes of Chiral Cyclams," *Tetra. Lett.*, vol. 29, No. 8, pp. 877–880, (1988).

Koola, et al., "Cobalt–Catalyzed Epoxidation of Olefins. Dual Pathways for Oxygen Atom Transfer", *J. Org. Chem.*, vol. 52, No. 20, pp. 4545–4553, (1987).

Lecas, A., "Synthese de la Meso–α β Bis(Diamino–2, 6 Phenyl) Octamethyl Porphyrine", *Tetra. Lett.*, vol. 25, No. 15, pp. 1563–1566, (1984).

Lee, et al., "Enantiomerically Pure Epoxychyomans via Asymmetric Catalysis", *Tetrahedron Letters*, vol. 32, No. 38, pp. 5055–5058, 1991.

Lee, et al., "Enantioselective Epoxidation of Conjugated Dienes and Enynes. Trans–Epoxides from Cis–Olefins", *Tetrahedron Letters*, vol. 32, No. 45, pp. 6533–6536, 1991.

Lee, et al., "Observations and comments on the mechanism of epoxidation of alkenes by manganese(III) porphyrins with hypochlorite", *Proc. Natl. Acad. Sci. USA* vol. 85, pp. 641–644, (Feb. 1988).

Leung, et al., "Oxidation Chemistry of Ruthenium–Salen Complexes," *Inorg. Chem.*, vol. 28, No. 26, pp. 4619–4622, (1989).

Mansuy, et al., "Asymmetric Epoxidation of Alkenes catalysed by a 'Basket–handle' Iron–Porphyrin bearing Amino Acids", *J. Chem. Soc., Chem. Commun.*, pp. 155–156, (1985).

Matsushita et al., "The Preparation and Characterization of Dichloromanganese(IV) Schiff Base Complexes," *Bull. Chem. Soc. Jpn.*, vol. 54, No. 9, pp. 2646–2651 (1981).

Mimoun, et al., "Selective Epoxidation of Olefins by Oxo [N–(2–oxidophenyl)salicylidenaminato]vanadium(V) Alkylperoxides. On the Mechanism of the Halcon Epoxidation Process", *J. Am. Chem. Soc.*, vol. 108, No. 13, pp. 3711–3718, (1986).

Minelli et al., "$^{95}$Mo NMR Measurements of Dioxomolybdenum(VI) Complexes. 3. Inverse Halogen Dependence of the Molybdenum Chemical Shifts of [$MoO_2^{2+}$] Complexes," *Inorg. Chem.*, vol. 23, No. 10, pp. 2554–2556, (1984).

Nakajima, et al., "Preparation and Characterization of Optically Active Schiff Base–Oxovanadium(IV) and –Oxovanadium(V) Complexes and Catalytic Properties of These Complexes on Asymmetric Oxidation of Sulfides into Sulfoxides with Organic Hydroperoxides," *Bull. Chem. Soc. Jpn.*, vol. 63, No. 9, pp. 2620–2630, (1990).

Nakajima, et al., "Asymmetric Oxidation of Sulfides to Sulfoxides by Organic Hydroperoxides with Optically Active Schiff Base–Oxovanadium (IV) Catalysts," *Chem. Lett.*, pp. 1483–1486, (1986).

Nakajima, et al., "Crystal Structure of a Binuclear N,N'–Disalicylidene–(R,R)–1,2–cyclohexanediamine–Titanium(IV) Complex and Asymmetric Oxidation of Methyl Phenyl Sulfide with Trityl Hydroperoxide Catalyzed by the Complex", *Chem. Lett.*, pp. 2189–2192, (1987).

Naruta, et al., "Synthesis of Chiral Twin Coronet Porphyrins and Catalytic and Asymmetric Epoxidation of Olefins," *Chem. Lett.*, pp. 1269–1272, (1989).

O'Malley et al., "Synthesis and Characterization of the Chiral Wall Porphyrin: A Chemically Robust Ligand for Metal–Catalyzed Asymmetric Epoxidations," *J. Am. Chem. Soc.*, vol. 111, pp. 9116–9117, (1989).

Ohta, et al., "Microbial Epoxidation of Long–chain Terminal Olefins", *J.C.S. Chem. Comm.*, 1978, pp. 849–850.

Okamoto, et al., "Effect of Catalyst on the Oxygenation of Styrene with $BH_4^-$ and Molecular Oxygen[1]", *Bull. Chem. Soc. Jpn.*, vol. 60, No. 12, pp. 4449–4450, Dec., 1987.

Pasini et al., "Optically Active Complexes of Schiff Bases. Part 4. An Analysis of the Circular–dichroism Spectra of Some Complexes of Different Co–ordination Numbers with Quadridentate Schiff Bases of Optically Active Diamines," *J. Chem. Soc.*, Dalton Trans., 346–356 (1977).

Saigo, et al., "Improved Optical Resolution of (±)–1, 2–Diphenylethylenediamine", *Bull. Chem. Soc. Jpn.*, vol. 59, pp. 931–932, (1986).

Samsel, et al., "Mechanism of the Chromium–Catalyzed Epoxidation of Olefins. Role of Oxochromium(V) Cations", *J. Am. Chem. Soc.*, vol. 107, No. 25, pp. 7606–7617, (1985).

Schurig, et al. "Enantioselective Epoxidation of Unfunctionalized Simple Olefins by Non–Racemic molybdenum–(VI)(oxo–diperoxo) Complexes," *J. Organometallic Chem.*, 370, pp. 81–96, (1989).

Schweizer et al., *Chromenes, Chromanones and Chromones*, Ch. II: 2H–and 4H–1–benzopyrans, pp. 11–139, (1977).

Sinigalia, et al., "Asymmetric Epoxidation of Simple Olefins Catalyzed by Chiral Diphosphine–Modified Platinum(II) Complexes", *Organometallics*, vol. 6, No. 4, pp. 728–734, (1987).

Srinivasan et al., "Epoxidation of Olefins with Cationic (Salen) $Mn^{III}$ Complexes. The Modulation of Catalytic Activity by Substituents," *J. Am. Chem. Soc.*, vol. 108, No. 9, pp. 2309–2320, (1986).

Takeichi, et al., "Asymmetric Cyclizations of Some Chlorohydrins Catalyzed by Optically Active Cobalt (Salen) Type Complexes", *Tetrahedron*, vol. 36, pp. 3391–3398, (1980).

Tani, et al., "Asymmetric Epoxidation of Hydrocarbon Olefins by Tert–Butyl Hydroperoxide With Molybdenum (VI) Catalysts in the Presence of Optically Active Diols. Application to the Asymmetric Synthesis of (3S)–2, 3–Oxidosqualene," *Tetra. Lett.*, No. 32, *Pergamon Press Ltd.*, pp. 3017–3020, (1979).

Wai, et al., "A Mechanistic Insight Leads to a Greatly Improved Osmium–Catalyzed Asymmetric Dihydroxylation Process," *J. Am. Chem. Soc.*, vol. 111, No. 3, pp. 1123–1125, (1989).

Yoon, et al., "Catalysis of Alkene Oxidation by Nickel Salen Complexes Using NaOCl under Phase–Transfer Conditions." *J. Am. Chem. Soc.*, vol. 110, pp. 4087–4089, (1988).

Yoon, et al., "High Turnover Rates in pH–Dependent Alkene Epoxidation Using NaOCl and Square–Planar Nickel(II) Catalysts," *J. Am. Chem. Soc.*, vol. 112, 4573–4574, (1990).

Zhang, "Asymmetric Olefin Epoxidation with Sodium Hypochlorite Catalyzed by Easily Prepared Chiral Mn(III) Salen Complexes," *Am. J. Org. Chem.*, vol. 56, No. 7, pp. 2296–2298, (1991).

Zhang, et al., "Enantioselective Epoxidation of Unfunctionalized Olefins Catalyzed by (Salen) manganese Complexes," *J. Am. Chem. Soc.*, vol. 112, No. 7, pp. 2801–2803, (1990).

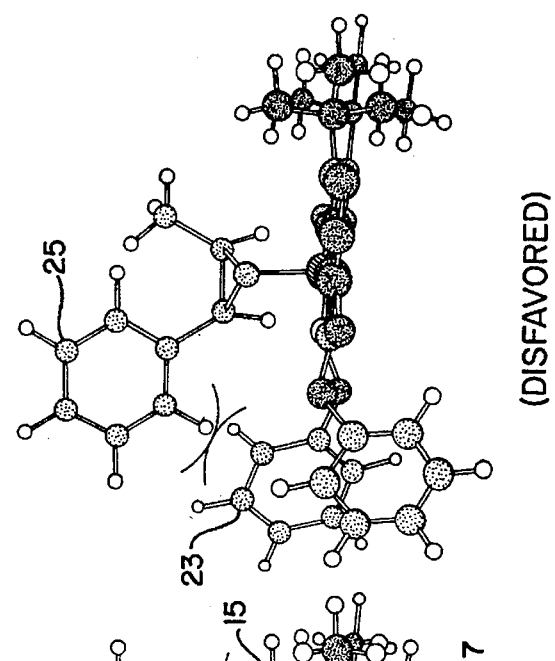
FIG. 5A (FAVORED)
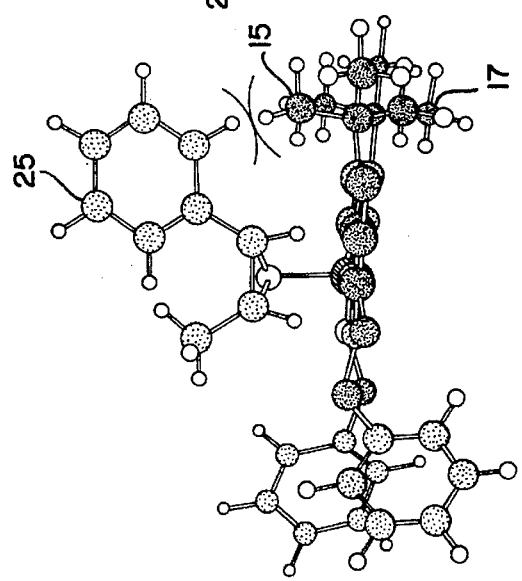
FIG. 5B (DISFAVORED)
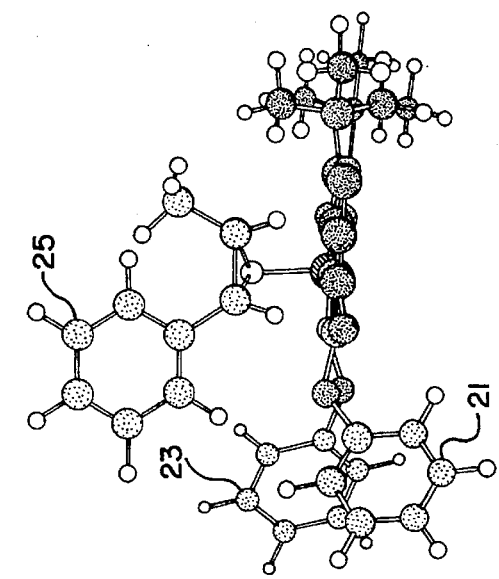
FIG. 5C (DISFAVORED)

5: $Y_1$ = OMe
6: $Y_1$ = t-Bu
7: $Y_1$ = Me
8: $Y_1$ = OMe

1: $Y_1$ = OMe
2: $Y_1$ = t-Bu
3: $Y_1$ = $NO_2$
4: $Y_1$ = H

CHIRAL CATALYSTS AND EPOXIDATION REACTIONS

CROSS-REFERENCE TO RELATED APPLICATION

The present application is a continuation of U.S. application Ser. No. 07/938,245 with a filing date of Oct. 15, 1992, now allowed, and which was nationalized from PCT Application No. PCT/US92/07261 filed Aug. 26, 1992, published as WO93/03838 Mar. 4, 1994, which PCT Application was a continuation-in-part U.S. patent application Ser. No. 07/809,446 filed Dec. 16, 1991, now abandoned, which application was in turn a continuation-in-part of U.S. patent application Ser. No. 07/749,460 filed Aug. 26, 1991, now abandoned, and of U.S. patent application Ser. No. 07/673,208 filed Mar. 21, 1991, now abandoned, which application was in turn a continuation-in-part of U.S. patent application Ser. No. 07/496,992 filed Mar. 21, 1990 and since abandoned.

STATEMENT OF GOVERNMENT INTEREST

This invention was made with Government support under Grant GM-43214-01A1 awarded by the National Institutes of Health and Grant CHE-9057740 awarded by the National Science Foundation. The government has certain rights in the invention.

BACKGROUND OF THE INVENTION

Chiral Catalysts and Catalysis

The present invention relates to the field of asymmetric catalysis. More particularly, the invention relates to the field of organometallic catalysts useful for enantioselectively epoxidizing prochiral olefins.

Several advances in catalysis of asymmetric group transfer have occurred in recent years. One such advance has been the discovery by K. B. Sharpless et al. of the epoxidation of allylic alcohols which provides access to enantiomerically pure synthetic building blocks. Unfortunately, Sharpless catalysis requires the presence of a specific functional group, namely an allylic alcohol, on the olefin to be epoxidized. Naturally, this requirement severely limits the variety of olefins which can be so epoxidized.

Some success has been achieved in asymmetric catalysis of unfunctionalized olefins. For example, K. B. Sharpless reported in 1988 that certain cinchona alkaloid derivatives were effective ligands in the osmium-catalyzed asymmetric dihydroxylation of trans-stilbene and various other olefins. This method provides a practical route to certain chiral diols, although cis olefins afford poor results.

Aside from the catalysts disclosed herein, it is believed that there currently exists no practical catalytic method for the asymmetric epoxidation of unfunctionalized olefins. Some progress has been made in this area through the use of chiral porphyrin complexes. In particular, J. T. Groves et al. reported in 1983 the asymmetric epoxidation of styrene by a chiral iron porphyrin catalyst. Unfortunately, the Groves system suffers several disadvantages, namely, the porphyrin catalyst is relatively difficult to prepare, oxidant proceeds to low substrate conversion, is limited to styrene derivatives, and achieves enantiomeric excess (ee) values of less than about 50 percent.

Epoxychroman Synthesis

Given the broad synthetic utility of epoxides, a simple, reliable, and practical procedure for asymmetric epoxidation of simple olefins is clearly desirable. One class of chiral epoxide with synthetic utility is the group of compounds generally known as epoxychromans, or epoxides of derivatives of chromene. For example, the epoxide of 6-cyano-2, 2-dimethylchromene has been found to be useful in the synthesis of a compound known as cromakalim. Two variations of cromakalim are shown in FIGS. 12 and 13. Both of these are believed to be potassium channel activators and have shown considerable promise as antihypertensive drugs.

As can be seen in FIGS. 12 and 13, the cromakalim compounds have two enantiomers. It is currently believed that only one of these enantiomers, namely the 3S, 4R enantiomer, possesses the antihypertensive activity. Consequently, a method of making a more enantiomerically pure epoxide of the precursor chromene derivative is highly desirable.

Taxol Synthesis

Taxol has emerged as a promising anti-cancer drug in preliminary clinical trials. However, taxol is a highly complex molecule which has not been fully synthesized and remains in short supply. Taxol may be considered to have two basic structural units, an N-benzoyl-3-phenyl-isoserine side chain and a highly functionalized diterpene nucleus. The tetracyclic ring structure of the nucleus represents by far the greater synthetic challenge, one that has as yet not been met despite the concerted efforts of several leading laboratories.

Consequently, a number of research groups are seeking semisynthetic routes of making taxol or analogs with taxol-like activity. Some of the new strategies involve side-chain synthesis and linkage to a naturally derived diterpene nucleus, or taxol congener.

A ready source of the taxol congener 10-deacetyl baccatin III (10-DB III) has been found. Chauviere, G., Guenard, D.; Picot, F.; Senilh, V.; Potier, P. C. R.: Seances Acad. Sci., Ser. 2, 293: 501–03, 1981. Denis et al. (J. Amer. Chem. Soc. 110:5417, 1988) developed a method of converting 10-DB III to taxol which utilizes, for the taxol C13 side chain, the protected form (2R, 3S)-N-benzoyl-O-(1-ethoxyethyl)-3-phenyl-isoserine. Denis, J.-N.; Greene, A. E.; Serra, A. A.; Luche, M.-J.J. Org. Chem. 51: 46–50, 1986.

A more efficient method of synthesizing an optically pure C13 side chain of taxol is desirable.

Chiral Catalysts and Oxidation of Sulfides

The present invention also relates to the field of organometallic catalysts useful for enantioselectively oxidizing sulfides to sulfoxides. Given the broad synthetic utility of surf oxides, a simple, reliable, and: practical procedure for asymmetric oxidation of sulfides is clearly desirable.

Asymmetric sulfide oxidation and olefin epoxidation strategies utilizing chiral oxaziridine derivatives have been developed with good to excellent success by Davis et al. Enantioselective catalysis of these reactions (and of asymmetric stoichiometric epoxidation)constitutes among the most interesting challenges in modem synthetic chemistry. To date, the only well-established and broadly successful methods for both these processes employ closely related Ti-tartrate-based catalysts with alkyl hydroperoxides as the terminal oxidant. Also, several chiral porphyrin complexes have been reported to catalyze both types of oxidation processes with modest selectivity using iodosylarenes as terminal oxidants.

Catalytic Disproportionation of Hydrogen Peroxide

The enzyme catalase, which occurs in blood and a variety of tissues decomposes hydrogen peroxide into oxygen gas and water very rapidly. This catalytic disproportionation of hydrogen peroxide (also known as the catalytic reaction) protects aerobic cells from oxidative stress and therefore is a biologically important process. Thus, it is desirable to find compounds which can function like catalase.

SUMMARY OF THE INVENTION

Briefly stated, the present invention is a chiral catalyst as well as a method of using said catalyst for enantioselectively epoxidizing a prochiral olefin.

In accordance with a first aspect of the invention, the chiral catalyst has the following structure:

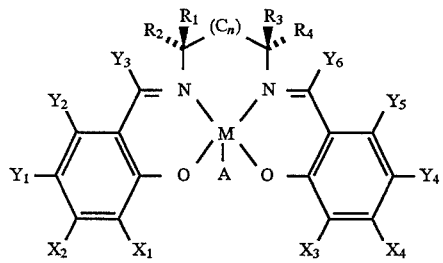

wherein M is a transition metal ion, A is an anion, and n is either 0, 1, or 2. At least one of X1 or X2 is selected from the group consisting of silyls, aryls, secondary alkyls and tertiary alkyls; and at least one of X3 or X4 is selected from the same group. Y1, Y2, Y3, Y4, Y5, and Y6 are independently selected: from the group consisting of hydrogen, halides, alkyls, aryl groups, silyl groups, and alkyl groups bearing hetero-atoms such as alkoxy and halide. Also, at least one of R1, R2, R3 and R4 is selected from a first group consisting of H, $CH_3$, $C_2H_5$, and primary alkyls. Furthermore, if R1 is selected from said first group, then R2 and R3 are selected from a second group consisting of aryl groups, heteroatom-bearing aromatic groups, secondary alkyls and tertiary alkyls. If R2 is selected from said first group, then R1 and R4 are selected from said second group. If R3 is selected from said first group, then R1 and R4 are selected from said second group. If R4 is selected from said first group, then R2 and R3 are selected from said second group.

In accordance with a second aspect of the invention, the chiral catalyst has the following structure:

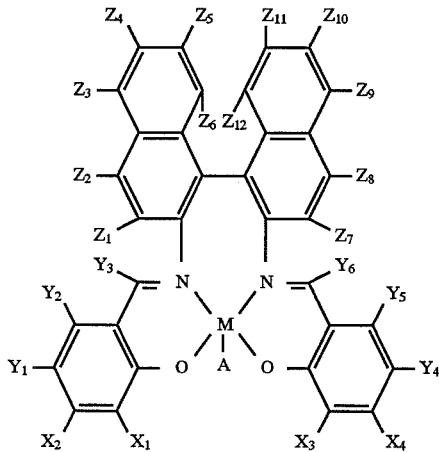

wherein M is a transition metal ion and A is an anion; where at least one of X1 or X2 is selected from the group consisting of aryls, primary alkyls, secondary alkyls, tertiary alkyls, and hetero atoms; where at least one of X3 or X4 is selected from the group consisting of aryls, primary alkyls, secondary alkyls, tertiary alkyls, and hetero atoms; and where Y1, Y2, Y3, Y4, Y5, Y6, Z1, Z2, Z3, Z4, Z5, Z6, Z7, Z8, Z9, Z10, Z11, and Z12 are independently selected from the group consisting of hydrogen, halides, alkyls, aryls, and alkyl groups bearing hetero atoms.

In accordance with a third, aspect of the invention, the chiral catalyst has the following structure:

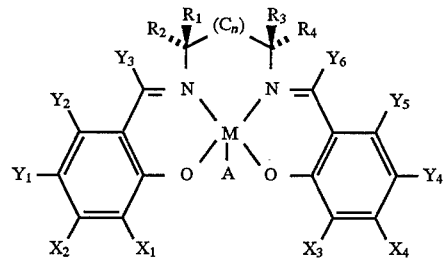

where M is a transition metal ion and A is an anion; where n is either 0, 1, or 2; where at least one of X1 or X2 is selected from the group consisting of aryls, primary alkyls, secondary alkyls, tertiary alkyls, and hetero atoms; where at least one of X3 or X4 is selected from the group consisting of aryls, primary alkyls, secondary alkyls, tertiary alkyls, and hetero atoms; where at least one of Y1 or Y2 is selected from the group consisting of aryls, primary alkyls, secondary alkyls, tertiary alkyls, and hetero atoms; where at least one of Y4 or Y5 is selected from the group consisting of aryls, primary alkyls, secondary alkyls, tertiary alkyls, and hetero atoms; where Y3 and Y6 are independently selected from the group consisting of hydrogen and primary alkyl groups; where either one or two of R1, R2, R3 and R4 is hydrogen; where, if R1 is hydrogen, then R3 is a primary alkyl; whore, if R2 is hydrogen, then R4 is a primary alkyl; where, if R3 is hydrogen, then R1 is a primary alkyl; and where, if R4 is hydrogen, then R2 is a primary alkyl.

In accordance with a fourth aspect of the invention, chiral catalyst has the following structure:

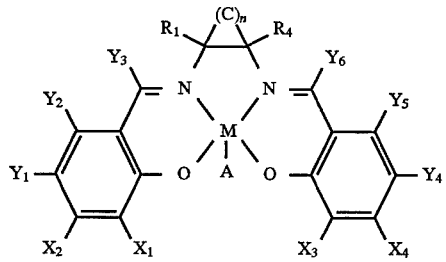

where M is a transition metal ion and A is an anion; where n is either 3, 4, 5 or 6; where at least one of X1 or X2 is selected from the group consisting of aryls, primary alkyls, secondary alkyls, tertiary alkyls, and hetero atoms; where at least one of X3 or X4 is selected from the group consisting of aryls, primary alkyls, secondary alkyls, tertiary alkyls, and hetero atoms; where at least one of Y1 or Y2 is selected from the group consisting of aryls, primary alkyls, secondary alkyls, tertiary alkyls, and hetero atoms; where at least one of Y4 or Y5 is selected from the group consisting of aryls, primary alkyls, secondary alkyls, tertiary alkyls, and hetero atoms; where Y3, and Y6 are independently selected from the group consisting of hydrogen and primary alkyl groups; where R1 and; R4 are trans to each other and at least one of R1 and R4 is selected from the group consisting of primary alkyls and hydrogen; and where the carbons in the $(C)_n$ portion have substituents selected from the group consisting of hydrogen, alkyl, aryl, and heteroatoms.

In accordance with the method aspect of the invention, a prochiral olefin, an oxygen atom source, and the chiral catalyst of one of the four aspects of the invention are reacted under such conditions and for such time as is needed to epoxidize said olefin.

In accordance with an alternate method aspect of this invention, a pyridine-N-oxide derivative is used. Preferably, 4-phenylpyridine-N-oxide or 4-t-butylpyridine-N-oxide is used. More preferably, 4-phenylpyridine-N-oxide is used.

The present invention of chiral catalysts and catalysis has provided certain advantages. First, the catalysts of the present invention provide a means for catalyzing the enantioselective epoxidation of mono, di, and tri-substituted olefins without the need for a specialized functional group on the olefin to interact with the catalyst. In other words, the catalysts of the present invention are particularly suited for catalyzing the asymmetric epoxidation of unfunctionalized olefins. This is in contrast to the prior art catalysts, such as the Sharpless catalyst, referred to above.

Second, the preferred catalysts of the invention show remarkable enantioselectively in catalyzing the epoxidation of cis, disubstituted olefins. See Example 1 below, where an ee of 85% was obtained with cis-β-methylstyrene when catalyzed with the most preferred embodiment of the first aspect. See also, the ee values for Example 12 which uses the most preferred catalyst of the fourth aspect of the present invention. As noted above, prior art catalysts have not provided ee values over 40% for cis, disubstituted olefins.

Third, the catalysts of the present invention are relatively easy to synthesize, particularly as compared to the porphyrin systems disclosed in the prior art.

Briefly stated, yet another embodiment of the present invention is a method of producing an epoxychroman using a chiral catalyst. In accordance with this method, a chromene derivative, an oxygen atom source, and a chiral catalyst from those described below are reacted under such conditions and for such time as is needed to epoxidize said chromene derivative.

The chromene derivative used in the present method has the following structure:

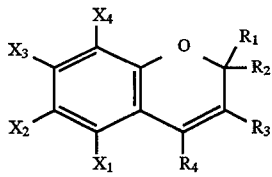

wherein R1, R2, R3, R4, X1, X2, X3, and X4 are each selected from the group consisting of hydrogen, aryls, primary alkyls, secondary alkyls, tertiary alkyls, and hetero atoms, and wherein no more than one of R1 and R2 are hydrogen.

The enantioselective method of producing an epoxychroman has provided certain advantages. First, the preferred catalysts of the invention show remarkable enantioselectivity in catalyzing the epoxidation of chromene derivatives. See Example 17 below, where an ee of 97% was obtained with the 6-cyano-2,2-dimethylchromene and the most preferred catalyst shown below. As noted above, prior art catalysts have not provided ee values over 40% for cis, disubstituted olefins.

Second, the present invention provides an effective and concise route to epoxychromans with very high enantioselectivity. Enantiomerically enriched epoxychromans are valuable intermediates for the synthesis of chiral 3,4-disubstituted chromans.

Third, the method is effective with a wide variety of substituted chromene derivatives.

Fourth, the catalysts of the present invention are relatively easy to synthesize, particularly as compared to the porphyrin systems disclosed in the prior art.

Yet another embodiment of the present invention is the method of enantioselectively producing a cis-epoxide of a cinnamate derivative using a chiral catalyst. In accordance with this method, a cis-cinnamate derivative, an oxygen atom source, and a chiral catalyst selected from those described below are reacted under such conditions and for such time as needed to epoxidize said cis-cinnamate derivative. Even more preferably, the reaction takes place in the presence of a pyridine-N-oxide derivative.

The cis-cinnamate derivative used in the present method has the following structure:

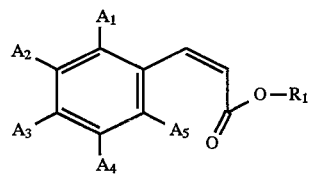

wherein A1–A5 are selected from the group consisting of hydrogen, aryls, primary alkyls, secondary alkyls, tertiary alkyls, hydroxyl, alkoxy groups, F, Cl, Br, I, and amines.

Still another embodiment of the present invention is the method of making a side chain of taxol or an analog thereof using a chiral catalyst. In accordance with this method, a cis-cinnamate derivative, an oxygen atom source, and a chiral catalyst selected from those described below are reacted under such conditions and for such time as needed to enantioselectively epoxidize said cis-cinnamate derivative. Even more preferably, the reaction takes place in the presence of a pyridine-N-oxide derivative. The cis-cinnamate derivative has the same structure as shown above.

The epoxide of the cis-cinnamate derivative is then regioselectively opened (i.e., preferentially breaking one particular oxygen bond) to produce 3-phenyl isoserinamide derivative. This 3-phenyl isoserinamide derivative is hydrolyzed to produce a 3-phenyl-isoserine derivative, which in turn is reacted with benzoyl chloride to form N-benzoyl-3-phenyl-isoserine derivative.

In yet another embodiment of this invention, taxol is synthesized using a chiral catalyst. In accordance with this method, an ethyl phenylpropiolate is partially hydrogenated to produce a cis-ethyl cinnamate. Then, the cis-ethyl cinnamate, an oxygen atom source, and a chiral catalyst selected from those described below are reacted under such conditions and for such time as needed to enantioselectively epoxidize said cis-ethyl cinnamate. Even more preferably, the reaction takes place in the presence of a pyridine-N-oxide derivative.

The epoxide of the cis-cinnamate is then regioselectively opened to produce 3-phenyl isoserinamide. This 3-phenyl isoserinamide is hydrolyzed to produce 3-phenyl-isoserine, which in turn is reacted with benzoyl chloride to form N-benzoyl-3-phenyl-isoserine. Next, the N-benzoyl-3-phenyl-isoserine is reacted with 1-chloroethyl ether and a tertiary amine in methylene chloride to form N-benzoyl-O-(1-ethoxyethyl)-3-phenyl-isoserine. Then, N-benzoyl-O-(1-ethoxyethyl)-3-phenyl-isoserine is reacted with the alcohol shown below:

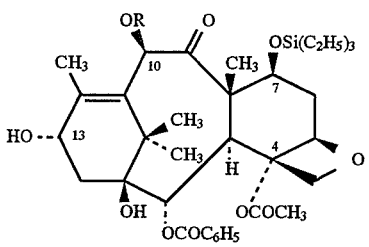

This resulting intermediate is converted to taxol by hydrolytically removing the 1-ethoxyethyl and triethylsilyl protecting groups.

The present method of enantioselectively synthesizing the side chain of taxol has certain advantages. The preferred catalysts of the invention show remarkable enantioselectively in catalyzing the epoxidation of cis-cinnamate derivatives. The synthesis may begin with relatively inexpensive ethyl phenylpropiolate. In particular, the addition of a pyridine-N-oxide derivative also increases the specificity and completion of the epoxidation.

Briefly stated, yet another embodiment of the present invention is a method of enantioselectively oxidizing sulfides using a chiral catalyst. In accordance with this method a sulfide, an oxygen atom source, and a chiral catalyst from those described below are reacted under such conditions and for such time as is needed to oxidize said sulfide. Preferably, the sulfide has the formula R1—S—R2 wherein R1 is any aromatic group and R2 is any alkyl group. Preferably, a cosolvent such as tetrahydrofuran, acetone or acetronitrile is employed. Also preferably, the oxygen atom source is either hydrogen peroxide or iodosylbenzene.

Still another embodiment of the invention is a method of catalytic disproportionation of hydrogen peroxide using a catalyst of the present invention. In accordance with this method, hydrogen peroxide and a catalyst selected from those described below are reacted under such conditions and for such time as is needed to disproportionate the hydrogen peroxide to dioxygen and water. Preferably, the catalyst is a monometallic (salen)Mn complex. Also preferably, the catalyst is mixed with a solvent such as EtOH, acetone, $CH_2Cl_2$, or $H_2O$.

The present invention, together with attendant objects and advantages, will be best understood with reference to the detailed description below read in conjunction with the accompanying figures.

BRIEF DESCRIPTION OF THE DRAWINGS

FIGS. 5A–5C are views similar to FIG. 4 illustrating the steric hindrance believed to be responsible for the high enantioselectivity observed in the epoxidation of one of the preferred substrates by the preferred catalysts of the present invention.

DETAILED DESCRIPTION OF THE PREFERRED EMBODIMENTS

As noted above, the present invention is a chiral catalyst as well as methods of using said those catalysts for enantioselectively epoxidizing prochiral olefins, chromene derivatives and cis-cinnamate derivatives.

The entire disclosures of U.S. patent application Ser. No. 809,446 filed Dec. 16, 1991 and U.S. patent application Ser. No. 749,460 filed Aug. 26, 1991, and of U.S. patent application Ser. No. 673,208 filed Mar. 21, 1991 which application was in turn a continuation-in-part of U.S. patent application Ser. No. 496,992 filed Mar. 21, 1990 are incorporated herein by reference.

The First Catalyst of the Invention

Figure 1:
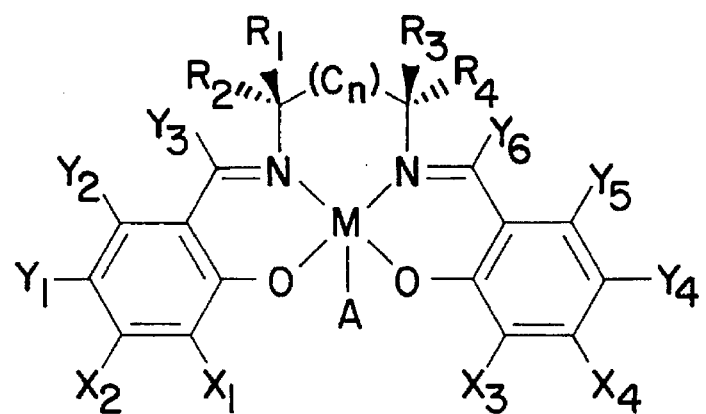
FIG. 1 shows the generalized 2-dimensional structure of a catalyst of the first aspect of the present invention.

FIG. 1 shows the structure of the first aspect of the present invention preferred chiral catalyst.

Figure 2:
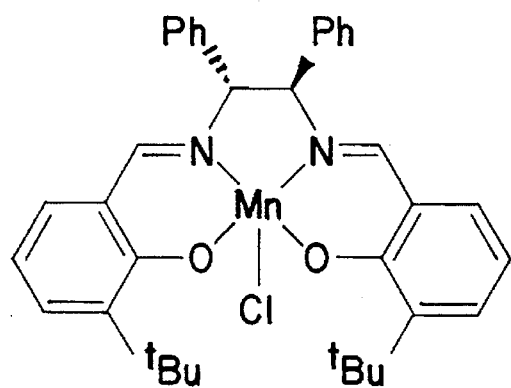
FIG. 2 shows the 2-dimensional structure of the most preferred catalyst of the first aspect of the present invention.

The preferred catalysts of the present invention are salen derivative-based complexes of a metal ion. The term "salen" is used herein to refer to those ligands typically formed through a condensation reaction of two molecules of a salicylaldehyde derivative with one molecule of a diamine derivative. While salen ligands are formed from ethylenediamine derivatives, propyl and butyl diamines may also be used to give analogous salpn and salbn derivatives. Salen derivatives are preferred and their general structure is shown in FIG. 1. A salen derivative where n is 0 is shown in FIG. 2.

As seen in FIG. 1, the two nitrogens and the two oxygens are oriented toward the center of the salen ligand and thus provide a complexing site for the transition metal ion M. Preferably, this metal ion is selected from the group consisting of Mn, Cr, Fe, Ni, Co, Ti, V, Ru, and Os. More preferably, the transition metal ion is selected from the group consisting of Mn, Cr, Fe, Ni, and Co. Most preferably, the metal ion is Mn.

The selection of the anion, A, is not seen to be critical to the performance of the catalyst. Preferably, the anion is selected from the group consisting of $PF_6$, $(aryl)_4$, $BF_4$, $B(aryl)_4$, halide, acetate, triflate, tosylate, with halide or $PF_6$ being more preferred, and chloride being most preferred.

FIG. 1 also shows the many sites available for substitution on the salen ligand. Of these sites, it is believed that R1, R2, R3, R4, and X1, X2, X3, X4, Y3 and Y6 are the most important in this first catalyst.

According to the first aspect of the invention, at least one of the X1 and X2 sites, and at least one of the X3 and X4 sites include a substituent selected from the group consisting of secondary or tertiary alkyl groups, aryl groups, silyl groups, and alkyl groups bearing heteroatom substituents such as alkoxy or halide. For reasons to be discussed below, these will be referred to as "blocking" substituents. Preferably, it is the X1 and X3 sites which bear one of these blocking substituents. More preferably, X1 and X3 bear the same substituent, which substituent is most preferably a tertiary alkyl group, such as tertiary butyl. Preferably, when X1 and X3 bear the blocking substituent, then X2 and X4 can be selected from a group of non-blocking substituents such as H, $CH_3$, $C_2H_5$, and primary alkyls, most preferably, H. Alternatively, either three or four of X1, X2, X3, and X4 can be selected from the group of blocking substituents.

According to this first aspect of the invention, at least one and no more than two of R1, R2, R3 and R4 are selected from a group consisting of H, $CH_3$, $C_2H_5$, and primary alkyls. For convenience, and consistent with the present theory to be discussed below, this group will be referred to as the non-blocking group. If R1 is selected from the non-blocking group, then R2 and R3 are selected from the blocking group. If R2 is selected from the non-blocking group, then R1 and R4 are selected from the blocking group. Likewise, if R3 is selected from the non-blocking group, then R1 and R4 are selected from the blocking group. Finally, if R4 is selected from the non-blocking group, then R2 and R3 are selected from the blocking group.

Stated in other tens, this first aspect of the invention requires that, of the four sites available for substitution on the two carbon atoms adjacent to nitrogen, either one or two of these will include a substituent from the non-blocking group. The invention also requires that the remaining sites include a substituent from the blocking group. In addition, it is a requirement that there not be two non-blocking substituents on the same carbon, and that there not be two non-blocking substituents on the same side on the two different carbons, i.e. not cis across the nitrogen.

Stated in yet another way, if there is only one non-blocking substituent, that non-blocking substituent can be on any one of the four substitution sites, R1, R2, R3, and R4, and the other three sites must include a blocking substituent. If, on the other hand, there are two non-blocking substituents, then they must be on different carbon atoms, and they must be trans to each other.

Preferably, the non-blocking substituent is either hydrogen or methyl, but most preferably, hydrogen. Preferably, the blocking substituent is either a phenyl group or a tertiary butyl group, but most preferably a phenyl group.

The substituents on the Y3 and Y6 sites affect the conformation of the ligand and thus have an influence on enantioselectivity in the epoxidation. Preferably, Y3 and Y6 are hydrogen, methyl, alkyl, or aryl. More preferably, they are hydrogen or methyl. Most preferably, they are hydrogen.

The Y1, Y2, Y4, and Y5 sites are seen to be less critical. Preferably, these sites are occupied by hydrogen, although these sites may also be occupied by substituents independently selected from the group consisting of hydrogen, halides, alkyls, aryls; alkoxy groups, nitro groups.

FIG. 2 shows the structure of the most preferred embodiment of this first aspect of the present invention catalyst. As can be seen, the most preferred substituent at X1 and X3 is a t-butyl group. Also, it is most preferred for the R1 and R4 sites to have the same blocking group, namely a phenyl group. In addition, it is most preferred to have the R2 and R3 sites occupied by a hydrogen. Finally, it is most preferred that the X2, X4, Y1, Y2, Y3, Y4, Y5, and Y6 sites are also all occupied by a hydrogen.

Figure 4:
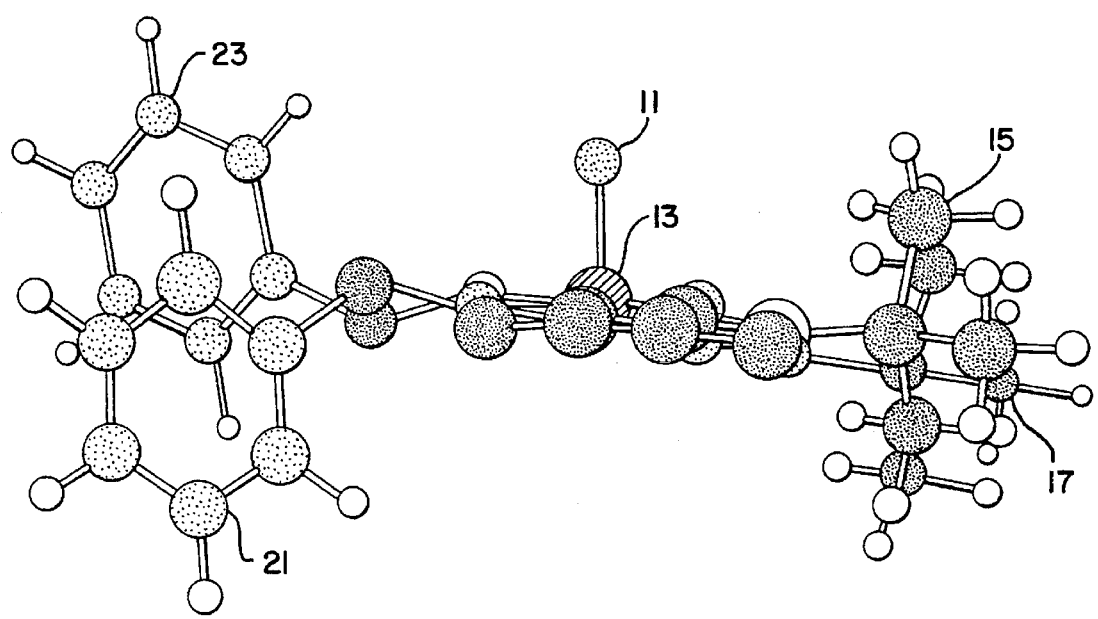
FIG. 4 is a computer generated 3-dimensional view of the most preferred catalyst of the present invention in its proposed oxo-intermediate state.

While not wishing to be bound by any particular theory, the following mechanism has been proposed to explain the remarkable enantioselectivity of the first aspect of the present invention catalyst. Referring to FIG. 4, which is a 3-dimensional view of the R,R enantiomer of the most preferred catalyst in its proposed oxo-intermediate state, it is seen that, with important exceptions, the salen ligand assumes a generally planar conformation with the oxygen atom 11 being complexed with the Manganese ion 13 and aligned on an axis generally perpendicular to this plane. The exceptions are the tert-butyl blocking groups attached at the X1 and X3 sites 15 and 17 respectively, and the phenyl blocking groups attached at the R1 and R3 sites 21 and 23, respectively. Although hard to depict in two dimensions, the phenyl blocking group 23 at R4 is behind the phenyl blocking group 21 at R1, while the R4 phenyl blocking group 23 is substantially above the plane of the catalyst and the R1 phenyl blocking group 21 is substantially below the plane of the catalyst.

FIGS. 5A–5C show the different transition orientations possible for a cis-disubstituted olefin, namely cis-methylstyrene, which are possible during epoxidation of the double bond.

FIG. 5A shows the favored orientation, i.e. the orientation with the least steric hindrance between the olefin and the blocking groups of the catalyst. This orientation results when the double bond approaches the oxygen atom from the front (as shown). This orientation results in the formation of the 1R,2S enantiomer of the cis-β-methylstyreneoxide.

FIG. 5B shows an orientation wherein methylstyrene has been rotated 180 degrees thus bringing the phenyl group of the styrene closer to the t-butyl groups 15 and 17 at the X1 and X3 positions. It is expected that steric hindrance between the phenyl group of the styrene 25 and the t-butyl groups 15 and 17 would disfavor this orientation.

FIG. 5C shows an orientation resulting from the double bond approaching the oxygen atom from behind (as shown). This orientation results in the formation of the 1S,2R enantiomer of the cis-β-methylstyrene oxide. In this orientation the phenyl group of the styrene 25 is closer to the phenyl group 23 on the R4 site. Steric hindrance between these two phenyl groups would thus disfavor this approach from behind the oxygen atom, and thus disfavor synthesis of the 1S,2R enantiomer.

In contrast, the orientation shown in FIG. 5A results from an approach from the front, i.e. the side where the R1 phenyl group 21 is below the plane of the catalyst, and thus not in the way. For this reason, the approach depicted in FIG. 5A is sterically favored, and thus synthesis of the 1R,2S enantiomer is favored.

It should be borne in mind that, although the above-described mechanism accurately predicts the high degree of enantioselectivity observed in the catalysts of the present invention, the mechanism is at present only a theory. As such, the proposed mechanism should in no way limit the scope of the present invention as defined by the appended claims.

It is noted that synthesis of the 1S,2R enantiomer of the cis-β-methylstyrene oxide is favored by using the S,S enantiomer of the catalyst.

It is also noted that this most preferred catalyst has $C_2$ symmetry, i.e. it is identical when rotated 180 degrees. Consequently, whether the oxygen atom is aligned on the top of the catalyst as shown, or the bottom of the catalyst, the result is exactly the same.

In alternative embodiments, the catalyst has only approximate $C_2$ symmetry. In particular, as per the rules described above, the groups are positioned on R1–R4 so that when rotated 180°, the blocking groups are in the same place and the non-blocking groups are in the same place. Consequently, the enantioselectivity of the catalyst is maintained because the oxygen can be complexed to either side of the catalyst while achieving roughly the same steric hindrances which favor the approach of the prochiral olefin from one side.

In other alternative embodiments, the catalyst has only one non-blocking group. As a result, there is a favored approach only when the oxygen is aligned on one side of the catalyst. Thus, the enantioselectivity of the catalyst is maintained.

The Second Aspect of the Invention

Figure 3:
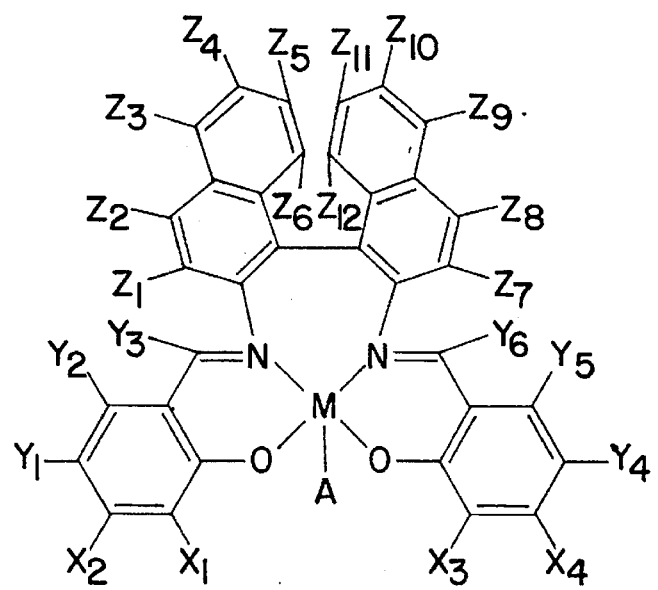
FIG. 3 shows the generalized 2-dimensional structure of the catalyst of the second aspect of the present invention.

In accordance with the second aspect of the present invention, the chiral catalyst is made with a binaphthyl diamine and has the following general structure (see also FIG. 3):

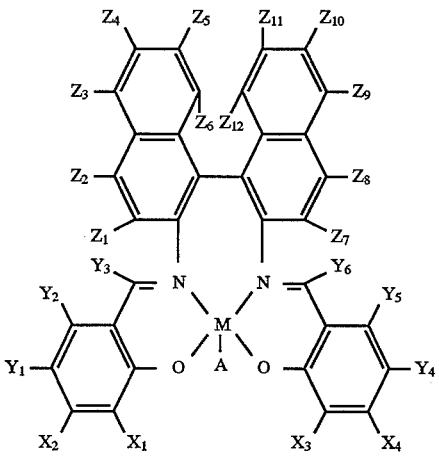

In this binaphthyl embodiment, the transition metal ion M and the anion A are preferably selected from the same group as that discussed above with FIG. 1. Also as above, it is required that at least one of X1 and X2 together with at least one of X3 and X4 are occupied by a group selected group of blocking substituents consisting of secondary or tertiary alkyl groups, aryl groups, silyl groups, and alkyl groups bearing heteroatom substituents such as alkoxy or halide. Preferably, it is the X1 and X3 sites which bear one of these substituents. More preferably, X1 and X3 bear the same substituent, which substituent is most preferably a tertiary alkyl group, such as tertiary butyl.

The substituents on the Y3 and Y6 sites affect the conformation of the ligand and thus have an influence on enantioselectivity in the epoxidation. Preferably, Y3 and Y6 are hydrogen, methyl, alkyl, or aryl. More preferably, they are hydrogen or methyl. Most preferably, they are hydrogen.

The substituents Z1 and Z2 affect the differentiation between the faces of the proposed metal oxo and thus have an influence on enantioselectivity in the epoxidation. Preferably, Z1 and Z2 are hydrogen, ethyl, alkyl, silyl, or aryl. More preferably, they are alkyl or aryl groups.

The Y1, Y2, Y4, and Y5 sites on the catalyst of this second aspect are also seen to be less critical. As above these sites are preferably occupied by hydrogen, although these sites may also be occupied by substituents independently selected from the group consisting of hydrogen, halides, alkyls, aryls, alkoxy groups, nitro groups.

As can be visualized, this binaphthyl alternative embodiment effects the same enantioselectivity as that of the preferred catalysts shown in the other figures. In particular, the configuration of the binaphthyl ligand provides for one of the naphthyl groups to be above the plane of the catalyst and the other naphthyl group to be below the plane of the catalyst, thereby favoring approach to the oxygen atom from one side.

The Third Aspect of the Invention

Figure 6:
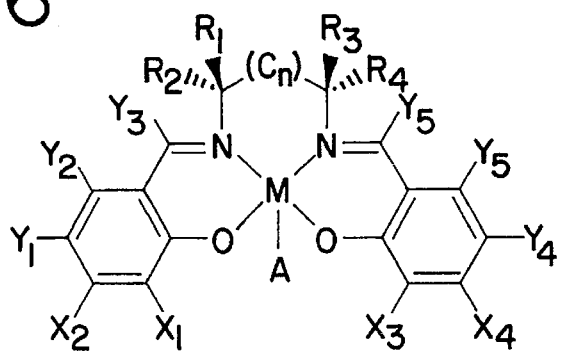
FIG. 6 shows the generalized 2-dimensional structure of the catalyst of the third aspect of the present invention.

FIG. 6 shows the structure of the third aspect of the present invention. In accordance with this aspect, the chiral catalyst has the following structure:

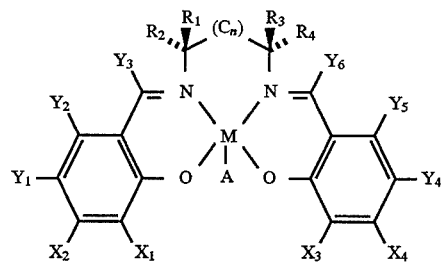

As with the first and second aspects, M is a transition metal ion selected from the group mentioned above, with Mn being the most preferred.

Likewise, A is an anion selected from the group mentioned above, with Cl being most preferred.

Also, n can be 0, 1, or 2, but 0 is the most preferred.

As with the first and second aspects, there is a blocking substituent on either X1 or X2 or on both. This blocking substituent is selected from the group consisting of aryls, primary alkyls, secondary alkyls, tertiary alkyls, and hetero atoms. There is also a blocking substituent selected from the same group on either X3 or X4 or on both. Preferably, the blocking substituents are at X1 and X3. More preferably they are the same group, and most preferably the blocking substituents are tert-butyl.

As a point of difference with the first aspect, the third aspect requires a blocking substituent located at the following positions: at least one of Y1 and Y2, and at least one of Y4 and Y5. Those blocking substituents are selected from the group as those for X1–X4, namely the group consisting of aryls, primary alkyls, secondary alkyls, tertiary alkyls, and hetero atoms. The importance of these "side" blocking substituents will be discussed below.

In this third aspect, substituents Y3 and Y6 are independently selected from the group consisting of hydrogen and primary alkyl groups. Preferably, Y3 and Y6 are hydrogen.

Also in this third aspect, at least one of R1, R2, R3 and R4 is hydrogen. Where R1 is hydrogen, R3 is a primary alkyl. Where R2 is hydrogen, R4 is a primary alkyl. Where R3 is hydrogen, R1 is a primary alkyl. Finally, where R4 is hydrogen, R2 is a primary alkyl. Preferably, R1 and R4 are both hydrogen and R2 and R3 are primary alkyls. Most preferably, R2 and R3 are methyl groups.

As can be seen, the catalyst of this third aspect is similar to the catalyst of the first aspect with the exception first the third aspect requires blocking substituents at the side positions of the catalyst, i.e. on the Y1 and/or Y2, and Y4 and/or Y5 sites. Also, either one or two of R1, R2, R3 and R4 is required to be an hydrogen, with the remaining substituents at the R sites required to be primary alkyls in the defined arrangement. The importance of this configuration and the proposed mechanism for the second catalyst are discussed below in connection with FIG. 10.

The Fourth Aspect of the Invention

Figure 7:
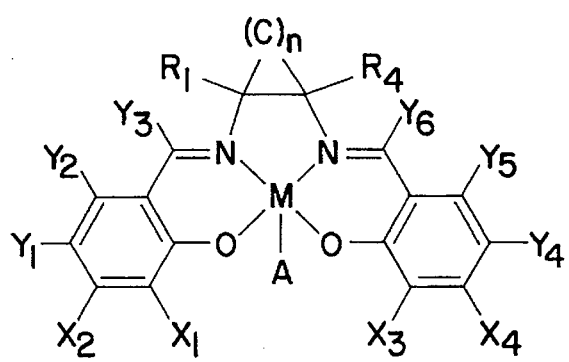
FIG. 7 shows the generalized 2-dimensional structure of a the catalyst of the fourth aspect of the present invention.

FIG. 7 shows the structure of a catalyst of the fourth aspect of the invention. This catalyst has the following structure:

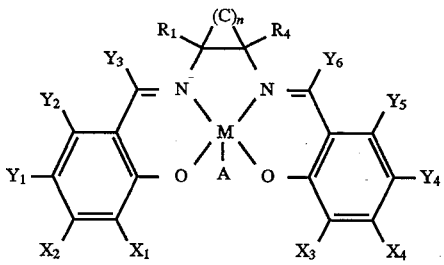

In this embodiment, the transition metal, M, and the anion, A, are selected from the same groups as above, with the same preferences.

Likewise, the substituents at X1, X2, X3, X4, Y1, Y2, Y4, and Y5 are selected from the same groups as in the second catalyst described above with the same preferences. In other words, this embodiment requires blocking substituents at the "bottom" and "sides" as does the second catalyst. Most preferably, X1, X3, Y1, and Y4 are all t-butyl.

The requirements and preferences for Y3 and Y6 are the same as with the third aspect. Preferably, Y3 and Y6 are hydrogen.

As can be seen, this catalyst of the fourth aspect of the invention includes a ting attached to the two nitrogen atoms, which ring is n+2 carbons long. In this catalyst, n can be 3, 4, 5 or 6. The carbons in the "$C_n$" portion can have substituents selected from hydrogen:, alkyl, aryl, and hetero atoms. Preferably, the substituents on the carbons in the "$C_n$" portion are hydrogen.

In this fourth aspect, R1 and R4 are configured so as to be trans to each other. Also, R1 and R4 are selected from the group consisting of primary alkyls and hydrogen. Preferably, R1 and R4 are the same. Most preferably, both R1 and R4 are hydrogen. Most preferably, this catalyst is used to epoxidize cis-cinnamate derivatives (see below).

Conceptually, the carbons in the ring which are adjacent the carbons which in turn are adjacent the nitrogen atoms are attached to what were shown as the R2 and R3 sites in the third aspect (FIG. 6). Thus, this fourth aspect is, in some respects, a subset of the third aspect with the two ends of the n carbon chain (a primary alkyl) being attached to the R2 and R3 sites.

Figure 8:
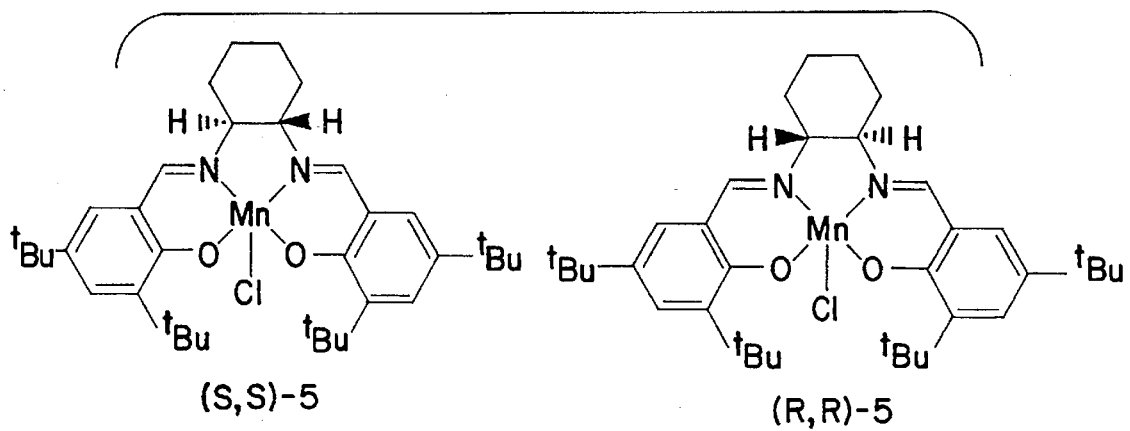
FIG. 8 shows the 2-dimensional structure of the preferred catalyst of the fourth aspect of the present invention.

One distinction between the third and fourth aspects is that the catalyst of the fourth aspect has R1 and R4 which can be either hydrogen or a FIG. 8 shows a preferred embodiment of this fourth aspect of the invention. As can be seen in this embodiment, the ring is six-membered, that is; n=4. Also, R1 and R4, which are trans to each other, are hydrogen. X1, X3, Y1, and Y4 are all t-butyl. All other substituents are hydrogen.

Figure 9:
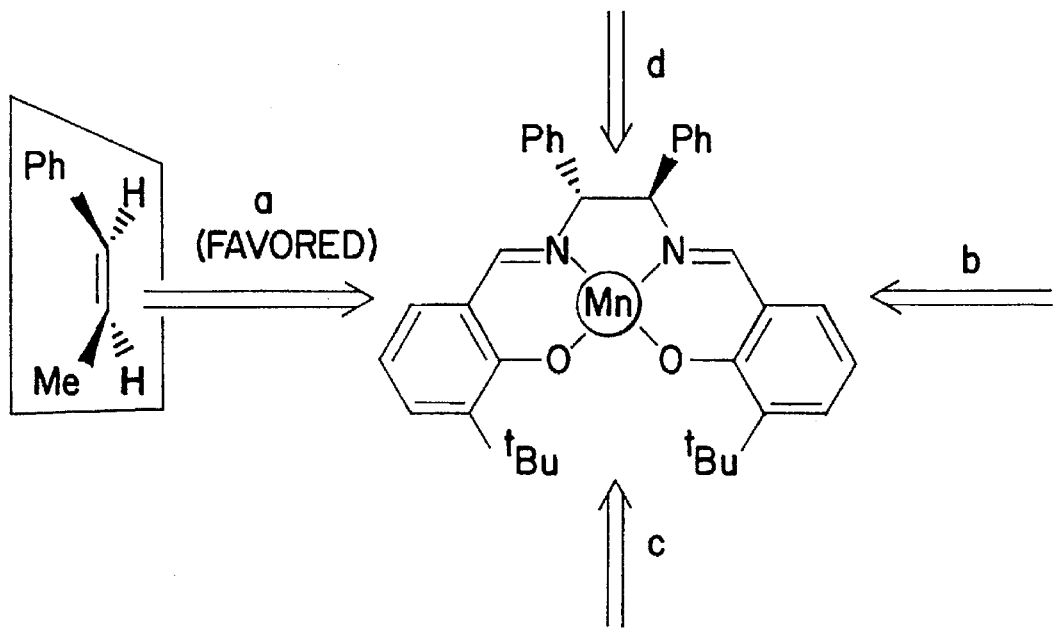
FIG. 9 is a 2-dimensional representation of the theorized favored approach of a prochiral olefin to a preferred catalyst of the fast aspect of the invention.
Figure 10:
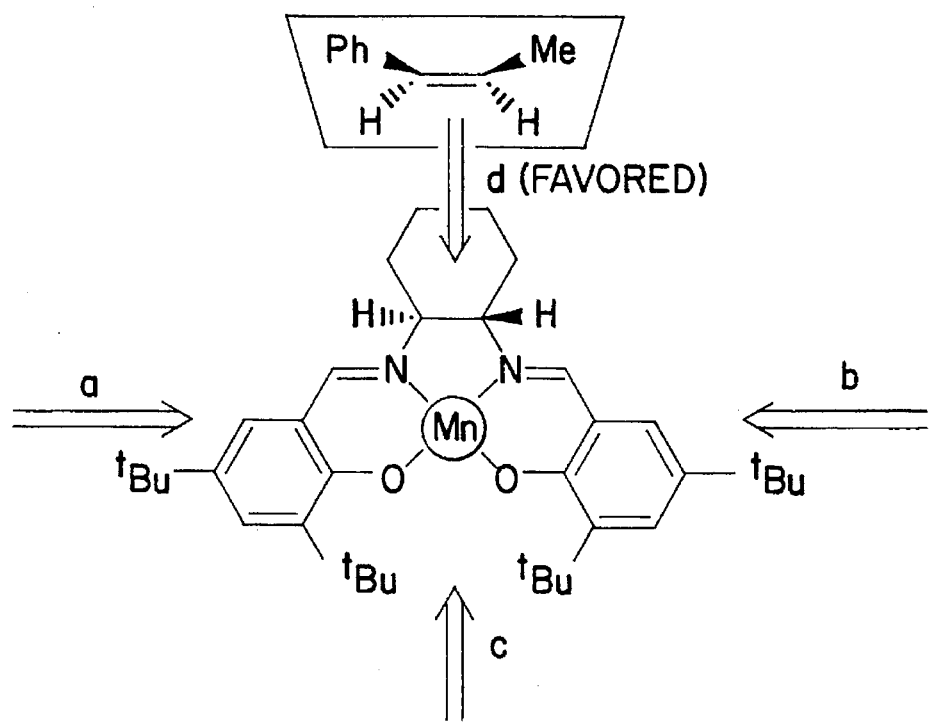
FIG. 10 is a 2-dimensional representation of the theorized favored approach of a prochiral olefin to a preferred catalyst of the second aspect of the invention.

FIGS. 9 and 10 illustrate the distinction between the mechanism proposed for the first and second aspects of the invention and the proposed mechanism for the third and fourth aspects.

FIG. 9, representing the first and second aspects, shows the proposed favored approach of the prochiral olefin. Approach c is believed to be disfavored by the bulky t-butyl groups. Approach d is similarly unfavorable, due to the steric bulk of the phenyl groups on the catalyst. Approaches a and b are differentiated by the dissymmetry of the catalyst. As shown in the depicted embodiment, because the phenyl to the left is below the page and the phenyl to the right is above the page, it is predicted that approach b will be less favorable due to steric interactions between the olefin and the phenyl group. In the context of the more favored approach from the left (approach a), it is predicted: that the more favorable approach of the olefin to the oxo group is such that the larger substituent on the olefin is oriented away from the t-butyl groups on the catalyst.

FIG. 10, representing the third and fourth aspects of the invention, shows the proposed favored approach of the olefin when the catalyst has side blocking groups. It is believed that, because of the side t-butyl groups at Y1 and Y4, the approaches a from the left and b from the right are disfavored. Likewise, because of the bottom blocking groups at X1 and X3, the approach c from the bottom is also disfavored. Thus, approach d from the top is favored. In addition, because of the chirality of the catalyst, the orientation of the prochiral olefin is also influenced. As shown in this depicted embodiment, because of greater steric hindrance on the right, the olefin is predicted to orient itself with the larger group on the left.

Because approach d is theorized to be the favored approach, the groups at R1 and R4 are limited to hydrogen and primary alkyls. In other words, it is believed that larger groups would block the approach d.

It should be noted that, although the above discussion is consistent with the observed results, the proposed mechanism for all four aspects of the invention is only theorized at this point. Consequently, the explanation is not to be viewed as limiting the scope of the invention as defined in the appended claims.

The preferred route to prepare the chiral catalysts of the present invention is a condensation reaction with the substituted salicylaldehyde and the substituted diamine. In general, quantities of these compounds are reacted in a 2 to 1 molar ratio in absolute ethanol. The solutions are refluxed typically for 1 hour, and the salen ligand is either precipitated in analytically pure form by addition of water, or the metal complex is generated directly by addition of the metal as its acetate, halide, or triflate salt.

The following procedure is general for the preparation of:

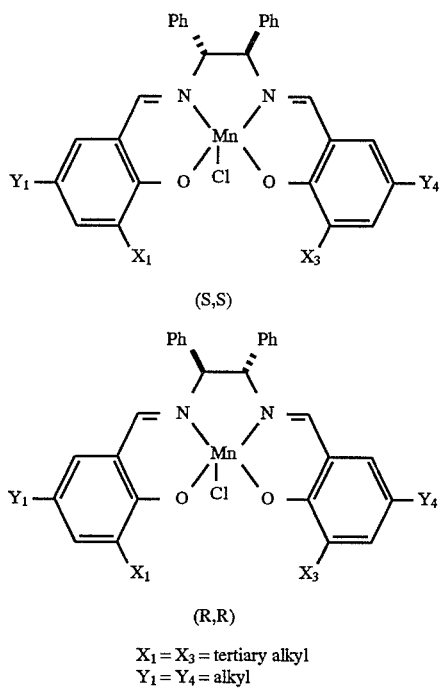

$X_1 = X_3$ = tertiary alkyl
$Y_1 = Y_4$ = alkyl

The salen ligand is redissolved in hot absolute ethanol to give a 0.1M solution. Solid $Mn(OAc)_2 \cdot 4H_2O$ (2.0 equivalents) is added in one portion and the solution is refluxed for 1 h. Approximately 3 equivalents of solid LiCl are then added and the mixture is heated to reflux for an additional 0.5 h. Cooling the mixture to 0° C. affords the Mn(III) complex 1 as dark brown crystals which are washed thoroughly with $H_2O$ and isolated by filtration in ≈75% yield. An additional crop of material can be obtained by dropwise addition of $H_2O$ to the mother liquor. Combined yields of catalyst are 89–96% for this step, and 81–93% overall from the optically pure 1,2-diphenylethylene diamine. Acceptable C, H, N, Cl, and Mn analyses of each of the catalysts have been obtained (±0.4%), although these vary according to the extent of water and ethanol incorporation in the powdery product. Enantioselectivities in the epoxidation reactions did: not vary among different batches of a given catalyst, indicating that the solvent content of the catalysts does not influence its effectiveness.

Another example of the method of preparing the catalyst is described as follows: Most preferably, the starting diamine is R,R- or S,S-1,2-diamino-1,2-diphenylethane and the starting salicylaldehyde is 3-tert-butylsalicylaldehyde.

A solution of 2.0 mmol of 3-tert-butylsalicylaldehyde in 3 ml of absolute ethanol is added dropwise to a solution of 1.0 mmol of (R,R)-1,2-diamino-1,2-diphenylethane in 5 ml of ethanol. The reaction mixture is heated to reflux for 1 h and then 1.0 mmol of $Mn(OAc)_2 \cdot 4H_2O$ is added in one portion to the hot (60° C.) solution. The color of the solution immediately turns from yellow to brown upon addition. It is refluxed for an additional 30 min and then cooled to room temperature. A solution of 10% NaCl (5 ml) is then added dropwise and the mixture stirred for 0.5 h. The solvents are then removed in vacuo and the residue is triturated with 50 ml of $CH_2Cl_2$ and 50 ml of $H_2O$. The organic layer is separated and the brown solution was washed with saturated NaCl. Separation of the organic phase and removal of solvent resulted in a crude material which was recrystallized from $C_6H_6/C_6H_{14}$ to give 0.938 mmol of the (R,R)-catalyst shown above (93.8%).

In accordance with the epoxidation method aspect of the invention, the prochiral olefin, an oxygen atom source, and the chiral catalyst are reacted under such conditions and for such time as is needed to epoxidize said olefin.

The prochiral olefin can be selected from monosubstituted, 1,1-disubstituted, cis-1,2-disubstituted, trans-1,2-disubstituted, trisubstituted, and tetrasubstituted. Of these, the monosubstituted and cis-1,2-disubstituted have shown the highest ee values.

Preferably, the prochiral olefin to be epoxidized is selected from the group consisting of cis-disubstituted olefins, including cyclic olefins, bearing a sterically demanding substituent on one end and a smaller substituent on the other end. More preferably, the prochiral olefin is a cis disubstituted olefin with a primary substituent on one side of the double bond and a secondary, tertiary, or aryl substituent on the other side.

The prochiral olefin can also be selected from the group consisting of enamines, enols, and alpha, beta-unsaturated: carbonyls. More preferably, the prochiral olefin is selected from the group consisting of cis-β-methyl-styrene, dihydronaphthalene, 2-cyclohexenyl-1,1-dioxolane, propylene, styrene and 2,2-dimethylchromene. Most preferably, the prochiral olefin is cis-β-methylstyrene.

The oxygen atom source used in the epoxidation reaction should be an oxidant which is relatively unreactive toward olefins under mild conditions. Preferably, the oxygen atom source is selected from the group consisting of NaOCl, iodosylmesitylene, $NaIO_4$, $NBu_4IO_4$, potassium peroxymonosulfate, magnesium monoperoxyphthalate, and hexacyanoferrate ion. More preferably, the oxygen atom, source is selected from the group consisting of NaOCl and iodosylmesitylen. For economic reasons, the most preferred oxygen atom source is NaOCl.

A preferred method uses NaOCl as the oxygen atom source. For convenience this method will be designated METHOD A. The details of METHOD A are as follows:

A solution of 0.05M $Na_2B_4O_7$ $10H_2O$ (1.0 mol) is added to a 2.5 ml solution of undiluted commercial household bleach (Chlorox). The pH of the resulting buffered solution is approximately 9.5, and it is adjusted to a pH of about 10.5 by addition of a few drops of 1M NaOH solution. To this solution is added a solution of 0.02 mmol of the preferred catalyst and 1.0 mmol of cis B methylstyrene in 2.0 ml of $CH_2Cl_2$. The two-phase mixture is stirred at room temperature and the reaction progress is monitored by capillary gas chromatography. After approximately 3 hours, 10 ml of $CH_2Cl_2$ is added to the mixture and the brown organic phase is separated, washed twice with 10 ml $H_2O$ and once with 10 ml saturated NaCl solution, and then dried for 15 minutes over anhydrous $Na_2SO_4$. The solution is filtered and solvent is removed under vacuum. The residue is purified by flash chromatography on silica gel using a 20:80 mixture of $CH_2Cl_2$:hexane as the eluting solvent. Pure epoxide is isolated as a colorless liquid in 70% yield (0.70 mmol) by combination of the product-containing fractions and removal of solvent under vacuum. The optical purity of this material is determined to be 85% ee by the method described below.

In a slightly less preferred embodiment, iodosylmesitylene is used as the oxygen atom source. For convenience, this method is designated as METHOD B and has the following preferred details: A solution of 1.0 mmol of olefin, 8 ml $CH_2Cl_2$ and 0.04 mmol of the catalyst are stirred at room temperature as solid iodosomesitylene is added in 0.3 mmol portions at 15–30 minute intervals. Disappearance of starting olefin is complete after addition of 6 portions (1.8 mmol) of total iodosylmesitylene. Solvent is removed in vacuo, the residue is extracted with hexane, and the mixture was filtered through Celite to remove catalyst and other solids. Pure epoxide was obtained by flash chromatography (10 g $SiO_2$, $CH_2Cl_2$/hexane 20:80 eluent). Enantiomeric excesses are determined by 1H NMR using $Eu(hfc)_3$ as a chiral shift reagent, or in the case of stilbene oxide by direct separation by HPLC on a commercial (Regis) covalently-bound leucine Pirkle column. Absolute configurations were assigned by comparison of αD with accepted literature values.

An alternative method also uses a pyridine-N-oxide derivative as a coordinating ligand, in addition to NaOCl as the oxygen source. More preferably, 4-phenylpyridine-N-oxide or 4-t-butylpyridine-N-oxide is used. Even more preferably, 4-phenylpyridine-N-oxide is used.

The trans-epoxide is a significant (about 25%) by-product of the epoxidation reaction. Preferably, the mixture of diastereomeric products is enriched in the desired cis- form by flash chromatography. Even more preferably, for large scale batches, no chromatography is not performed.

The next steps are shown in Scheme 2.

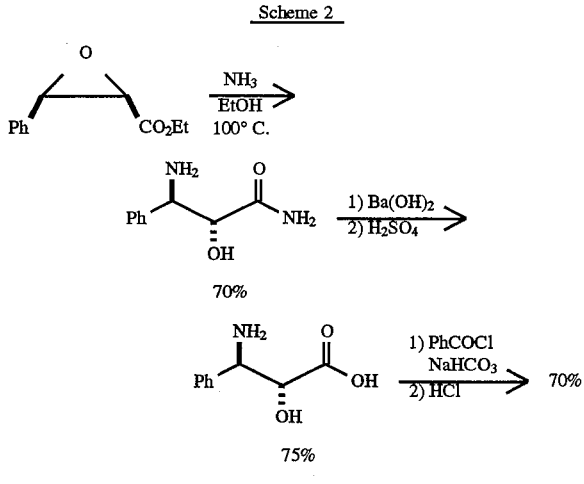

The epoxide mixture is reacted with ammonia in ethanol, which results in regioselective ring-opening to the desired 3-phenyl-isoserine amide derivative. Preferably, very little regioisomer is detected in the crude amide mixture by $^1H$ NMR. Next, diastereomerically pure 3-phenyl-isoserine is isolated by recrystallized of the crude product mixture. For convenience this method will be designated METHOD C. The details of METHOD C are as follows:

A solution of 0.05M $Na_2B_4O_7 \cdot 10H_2O$ (1.0 ml) or other suitable buffer such as phosphate is added to a 2.5 ml solution of undiluted commercial household bleach (Chlorox®). The pH of the resulting buffered solution is approximately 9.5, and it is adjusted to a pH of about 10.5–11.5 by addition of a few drops of 1M NaOH solution and cooled in an ice bath to about 0°–4° C. A separate solution of 10 mmol of alkene and 2.0 mmol (or 20 mol %) of a pyridine-N-oxide derivative are dissolved in 10 ml of $CH_2Cl_2$. Next, 0.05–0.6 mmol (0.5–6 mol %) of catalyst 1 or 2 were added to the alkene solution and

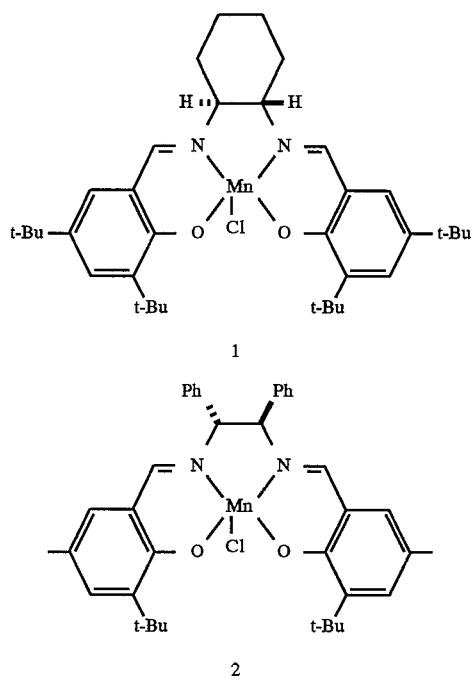

cooled separately in an ice bath. When the two solutions were at 0°–4° C., they were combined, and the two-phase mixture was stirred. The reaction progress was monitored by capillary gas chromatography. After about one to five hours, 200 ml of hexane was added to the mixture and the organic phase was separated, washed twice with 100 ml $H_2O$ and once with 100 ml saturated. NaCl solution, and then dried for 15 minutes over anhydrous $Na_2SO_4$. The solution is filtered and solvent is removed under vacuum. The residue is purified by chromatography, distillation or crystallization. Pure epoxides were isolated, and the optical purity of the materials were determined as described in more detail below.

Method of Chromene Epoxidation

As noted above, the present invention is a method of using a chiral catalyst to epoxidize a chromene derivative, thus producing an epoxychroman. The structure of the chromene derivative is as follows:

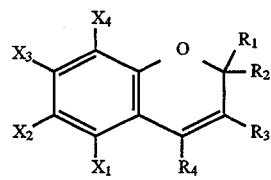

wherein R1, R2, R3, R4, X1, X2, X3, and X4 are each selected from the group consisting of hydrogen, aryls, primary alkyls, secondary alkyls, tertiary alkyls, and hetero atoms, and wherein no more than one of R1 and R2 are hydrogen.

It has been found that when beth R1 and R2 are hydrogen, i.e. when the chromene is not substituted at the R1 and R2 locations, the epoxide is not formed (see Example 24 below).

Preferably, R1 and R2 are the same group. In this situation the chromene derivative is prochiral.

Also, the chromene-derivative preferably includes an alkyl group at both R1 and R2. More preferably, the chromene derivative includes a methyl group at R1 and R2.

Most preferably, the chromene derivative is 6-cyano-2,2-dimethylchromene, namely the precursor for making cromakalim. As mentioned above, this most preferred chromene derivative can be epoxidized with a remarkably high degree of enantioselectivity to the epoxychroman useful in producing enantiomerically pure cromakalim (see Example 17 below).

As noted above, this embodiment of de present invention has been found to produce remarkable enantioselectivity in the epoxidation of chromene derivatives. In addition, the catalysts of the present invention have been found to provide remarkably high yields (See Examples 17–23, and 25 below). The catalyst of the fourth aspect (FIG. 8) above is the most preferred catalyst used in the present method. Experiments have shown that when a racemic mixture of the chiral catalysts are used in the reaction that relatively high yields of a racemic mixture of the epoxychromans are achieved. Consequently, in accordance with a less preferred embodiment of the invention, when a racemic mixture of the epoxychromans is desirable or acceptable, a racemic mixture of the chiral catalyst is used with the chromene derivatives. Nevertheless, because enantiomerically pure epoxychromans are typically highly desirable, particularly as synthetic precursors, enantiomerically pure chiral catalysts are clearly preferred.

In accordance with the epoxychroman synthetic method of the present invention, the chromene derivative, an oxygen atom source, and the chiral catalyst are reacted under such conditions and for such time as is needed to epoxidize said chromene derivative. Alternatively, a pyridine-N-oxide derivative is added to the reaction mixture.

The oxygen atom source used in the epoxidation reaction should be an oxidant which is relatively unreactive toward olefins under mild conditions. Preferably, the oxygen atom source is selected from the group consisting of NaOCl, iodosylmesitylene, NaIO$_4$, NBu$_4$IO$_4$, potassium peroxymonosulfate, magnesium monoperoxyphthalate, H$_2$O$_2$, peroxybenzoic acid derivatives, and hexacyanoferrate ion. More preferably, the oxygen atom source is selected from the group consisting of NaOCl and iodosylmesitylene. For economic reasons, the most preferred oxygen atom source is NaOCl.

In the most preferred method for chromene epoxidation, NaOCl is the oxygen atom source, as described above for METHOD A. In a slightly less preferred embodiment, iodosylmesitylene is used as the oxygen atom source, as described above for METHOD B. Alternatively, a pyridine-N-oxide derivative and NaOCl are used, as described in METHOD C.

Method of Epoxidation of cis-Cinnamate Derivatives and Preparation of Taxol Intermediates and Analogs As a first step in the synthesis of the C-13 side chain of taxol, commercially available ethyl phenylpropiolate is partially hydrogenated to cis-ethyl cinnamate over commercial Lindlar's catalyst (Scheme 1 below). Because the reaction was observed to be more enantioselective, ethyl phenylpropiolate is preferred over methyl phenylpropiolate as a starting material.

Scheme 1

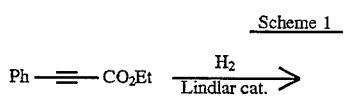

-continued
Scheme 1

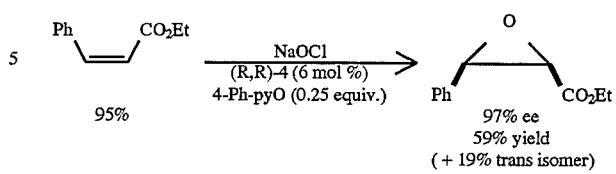

The cis-ethyl cinnamate thus obtained has been observed to contain small amounts (about 5%) of overreduced material and starting alkyne. However, these impurities do not appear to interfere with subsequent steps and are easily removed later in the synthetic sequence.

Next, cis-ethyl cinnamate is epoxidized with commercial bleach in the presence of one of the chiral catalysts discussed above as the first, second third and fourth embodiments of the invention. Most preferably, the fourth embodiment of the invention (the (R,R)5 catalyst of FIG. 8) is employed and is shown below:

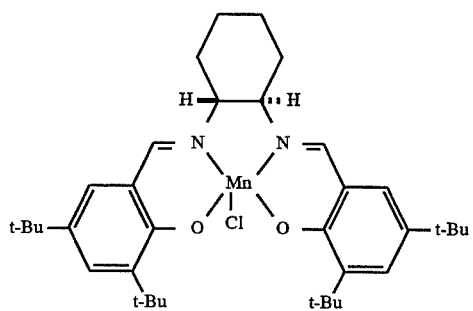

In the presence of this enantioselective catalyst, the cis-ethyl cinnamate was observed to epoxidize to the (R,R)-(+) enantiomer of the cis-epoxide.

Preferably, 4-phenylpyridine-N-oxide is added to the epoxidation mixture. This coordinating ligand appears to markedly enhance reaction completion and enantioselectivity. With the use of 4-phenylpyridine-N-oxide, the (R,R)-(+)-enantiomer of cis-ethyl cinnamate epoxide was in excess of 96–97%. Either a less preferred pyridine-N-oxide derivative, or 4-t-butylpyridine-N-oxide may be used, but 4-phenylpyridine-N-oxide is preferred.

The trans-epoxide is a significant (about 25%) by-product of the epoxidation reaction. Preferably, the mixture of diastereomeric products is enriched in the desired cis- form by flash chromatography. Even more preferably, for large scale batches, no chromatography is not performed.

The next steps are shown in Scheme 2 below.

Scheme 2

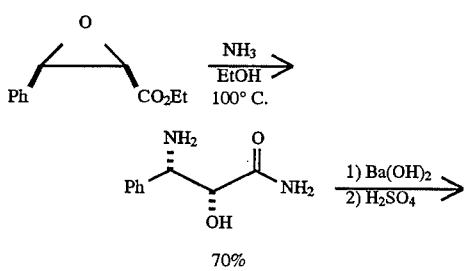

-continued
Scheme 2

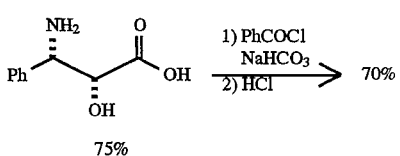

75%

The epoxide mixture is reacted with ammonia in ethanol, which results in regioselective ring-opening to the desired 3-phenyl-isoserine amide derivative. Very little regioisomer has been detected in the crude amide mixture by $^1$H NMR. Next, diastereomerically pure 3-phenyl-isoserinamide was isolated by recrystallization of the crude product mixture.

The 3-phenyl-isosorinamide is hydrolyzed to remove the amide group. Preferably, the hydrolysis is effected without epimerization. Even more preferably, the hydrolysis is effected by using Ba(OH)$_2$ in water.

Next, the hydrolyzing salt is acidified and precipitated. Preferably, if Ba(OH)$_2$ salt is used for hydrolysis, it is next precipitated out of the solution by addition of sulfuric acid.

Next, 3-phenyl-isoserine is obtained directly by crystallization of the product mixture. This enantiomerically enriched 3-phenyl-isoserine is used to prepare a wide variety of taxol analogs. Preferably, the taxol side chain benzoyl derivative is prepared from 3-phenyl-isoserine.

The taxol side chain is prepared by adding to the 3-phenyl-isoserine formed above benzoyl chloride and sodium bicarbonate in an acid two-phase reaction. Subsequently, the benzoic acid by-product is extractively removed by stirring the solid product mixture with ether and ethanol. Finally, pure N-benzoyl-3-phenyl-isoserine is collected by filtration. The material thus obtained was determined by polarimetry to have an ee of more than 97% and to have the same absolute configuration as the side chain from natural taxol.

The N-benzoyl-3-phenyl-isoserine is reacted to produce N-benzoyl-O-(1-ethoxyethyl)-3-phenyl-isoserine, which in turn is reacted with a tertiary amine activating agent and 7-triethylsilyl baccatin III to form a C-2', C-7-protected taxol derivative. This derivative is treated with acid in ethanol to produce taxol.

While not wishing to be bound by this theory, it appears that 4-phenylpyridine-N-oxide effectively increases the success of the enantiomerically selection and complete epoxidation of cis-ethyl cinnamate to the (R,R)-(+)-enantiomer of the cis-epoxide. In the absence of 4-phenyl-pyridine-N-oxide, epoxidation is 10–15% less selective and is less complete, even when 15–20 mol % more catalyst is used. Control experiments indicated that the pyridine-N-oxide derivative did not act as the oxygen-atom source, but rather as a coordinating ligand. It appears that coordination of pyridine-N-oxide derivative to the mildly Lewis acidic Mn(III) and/or Mn(V) oxo intermediate helps prevent the metallic center from remaining complexed with the carbonyl functionality on the substrate in a non-product coordination mode. Thus, the pyridine-N-oxide derivative appears to prevent decomposition reactions and improve catalyst stability with certain olefins, although not all olefins.

The enantioselectivity of the reaction was also found to be quite sensitive to the identity of the ester group on the starting material, with cis-methyl cinnamate being epoxidized under similar conditions as cis-ethyl cinnamate, but in only 87–89% enantiomeric excess.

The advantages of this synthetic method are that it begins with commercially available ethyl phenylpropiolate and employs hydrogen gas, household bleach, ammonia and barium salts as stoichiometric reagents. Another advantage is the high optical and chemical purity of N-benzoyl-3-phenyl-isoserine. As will become apparent in the examples 29 to 39 below, the yields of each of the individual steps are acceptable for a commercially feasible process, even though they have not yet been completely optimized. The catalytic specificity, procedural simplicity, inexpensive reagents and avoidance of preparative chromatographic separations renders this synthetic method a most practical route to enantiomerically pure 3-phenyl-isoserine derivatives.

Method of Sulfide Oxidation

As noted above, the present invention is a method of using a chiral catalyst to enantioselectively oxidize a sulfide to a sulfoxide. The method involves reacting a sulfide, an oxygen atom source, and a chiral catalyst under the proper conditions to oxidize the sulfide. Preferably the sulfide has the formula R1—S—R2 where R1 is any aromatic group and R2 is any alkyl group. Preferably, the oxygen atom source is hydrogen peroxide or iodosylbenzene and preferably, a cosolvent such as tetrahydrofuran, acetone, or acetonitrile is used.

As described above, for enantioselective epoxidation by the (salen)Mn catalysts, aqueous sodium hypochlorite was used as the stoichiometric oxidant. However, the reaction between sulfides and sodium hypochlorite was too rapid for this oxidant be useful for enantioselective sulfide oxidation reactions. Iodosylbenzene was tried because iodosylarenes react slowly with sulfides. It was found that iodosylbenzene did indeed serve as an effective oxygen atom source. However, iodosylarenes are impracticable as stoichiometric oxidants due to their instability in the solid state, their lack of solubility, their relatively high cost and the high molecular weight of the byproduct of oxygen transfer, an iodoarene.

Hydrogen peroxide was determined to be a good oxidant for sulfide oxidation. Hydrogen peroxide gave higher yields of sulfoxide, minimal overoxidation to sulfone and identical enantioselectivities to those observed with iodosylbenzene. This suggests that both oxidants generate a common Mn(V) oxo reactive intermediate.

To facilitate the reaction, a cosolvent was used. The cosolvent minimized the catalase-decomposition of hydrogen peroxide by the catalysts and a complete conversion of sulfide was accomplished with less than 6 equivalents of oxidant.

Figure 20:
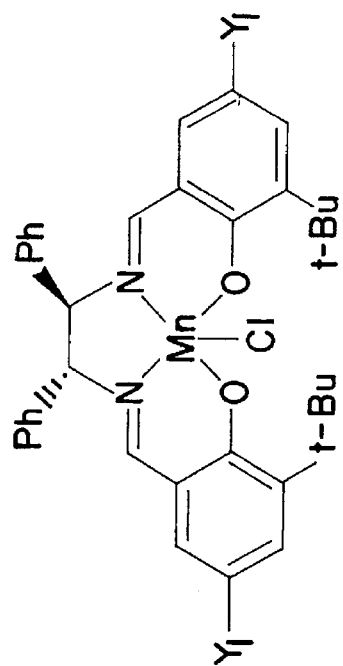
FIG. 20 shows the structure of another preferred chiral catalyst used in asymmetric sulfide oxidation.
Figure 19:
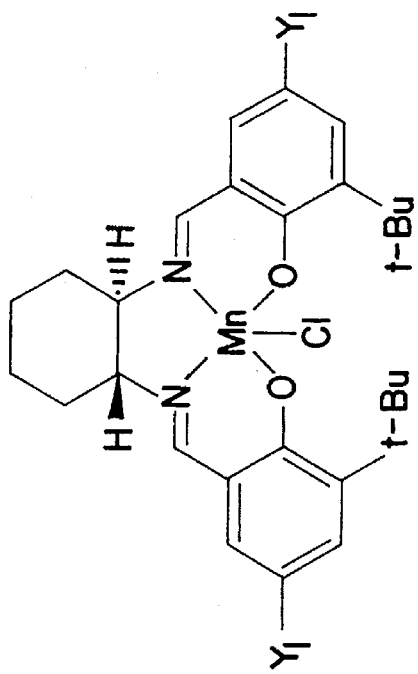
FIG. 19 shows the structure of a preferred chiral catalyst used in asymmetric sulfide oxidation.

Generally, catalysts derived from 1,2-diaminocyclohexane and 1,2-diphenylethylene diamine were more selective than those prepared from other synthetically less accessible diamines. FIGS. 19 and 20 show the structures of the preferred catalysts. Specific catalysts based on these, were tested for asymmetric sulfide oxidation and Example 40 lists the results of the tests.

Catalytic Disproportionation of Hydrogen Peroxide

As mentioned above, the decomposition of hydrogen peroxide into oxygen and water is a biologically important process. All of the catalysts described so far are useful in the catalytic disproportionation of hydrogen peroxide. However, for this particular reaction, the catalysts do not have to be chiral. Thus, any catalyst having the following formula will function in the decomposition reaction:

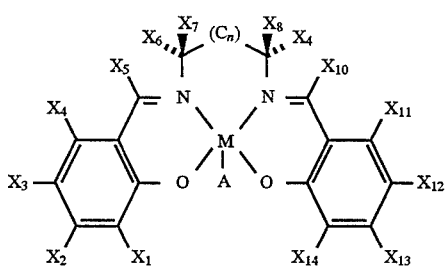

wherein M is a transition ion, A is an anion, n is either 0, 1, or 2 and X1 through X14 are independently selected from the group consisting of hydrogen, halides, alkyls, aryls and alkyl groups bearing hereto atoms.

The catalysts of the present invention are stable, easy to synthesize, have a low molecular weight and a high catalytic activity. In fact their catalytic activity is comparable to any synthetic catalase mimic developed to date. The preferred catalysts are the monometallic (salen)Mn complexes shown in FIGS. 22 and 23.

To carry out the disproportionation reaction, the catalyst is mixed with a solvent such as EtOH, acetone, $CH_2Cl_2$, or $H_2O$ and then hydrogen peroxide is added.

EXAMPLES

The following examples are provided by way of explanation and illustration. As such, these examples are not to be viewed as limiting the scope of the invention as defined by the appended claims.

Preparation of the Catalysts
Procedures for the Preparation of Chiral Salen Based Catalysts
Preparation of:

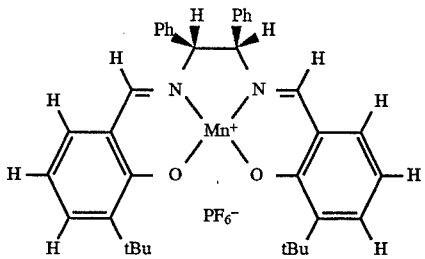

(R,R)-1,2-Diphenyl-1,2-bis(3-tert-butyisalicylideamino) ethane (2)

A solution of 360.5 mg (2.0 mmol) of 3-tertbutylsalicylaldehyde in 3 ml of EtOH was added dropwise to a solution of 212.3 mg (1.0 mmol) of (R,R)-1,2-diamino-1,2-diphenylethane in 5 ml of EtOH. The reaction mixture was heated to reflux for 1 h and water (5 ml) was added. The oil that separated solidified upon standing. Recrystallization from MeOH/$H_2O$ gave 485.8 mg (91%) of yellow powder, mp 73°–74° C. $^1$H NMR (CDCl$_3$) δ 1.42 (s, 18H, CH$_3$), 4.72 (s, 2H, CHN=C), 6.67–7.27 (m, 16H, ArH), 8.35 (s, 2H, CH=N), 13.79 (s, 2H, ArOH) ppm; 13C NMR (CDCl$_3$) δ 29.3, 34.8, 80.1, 117.8, 118.5, 127.5, 128.0, 128.3, 129.6, 130.1, 137.1, 139.5, 160.2, 166.8 ppm. Anal. Calcd. for $C_{36}H_{40}N_2O_2$. C, 81.17; H, 7.57; N, 5.26. Found: C, 81.17; H, 7.60; N, 5.25.

((R,R)-1,2-Diphenyl-1,2-bis(3-tert-butylsalicylideamino) ethane)manganese(II) Complex (3)

Under strictly air-free conditions, a solution of 64.0 mg (1.6 mmol) of NaOH in 2 ml of MeOH was added dropwise to a solution of 426. 1 mg (0.8 mmol) of (2) in 5 ml of EtOH with stirring under an atmosphere of nitrogen. A solution of 196.1 mg (0.8 mmol) of Mn(OAc)$_2$•4H$_2$O in 3 ml of MeOH was added rapidly and the orange mixture was stirred for 24 hr. The solvent was removed in vacuo and the residue was stirred with 5 ml of benzene and filtered to remove. NaOAc. The filtrate was concentrated to about 1 ml and 3 ml of hexane was added. The mixture was cooled to –30° C. and the precipitate was collected by filtration to give 410.2 mg (87%) of orange powder. Anal. Calcd. for $C_{36}H_{38}MnN_2O_2$—(CH$_3$OH) 0.5; C, 72.86; H, 6.70; N, 4.66. Found.: C, 73.05; H, 6.76; N, 4.39.

((R,R)-1,2-Diphenyl-1,2-bis(3-tert-butylsalcylideamino) ethane)manganese(III) Hexafluorophosphate ((R,R)-1)

A solution of 165.5 mg (0.05 mmol) of ferrocenium hexafluorophosphate in 2 ml of CH$_3$CN was added dropwise to a solution of 292.8 mg (0.05 mmol) of (3) in 3 ml of CH$_3$CN under N$_2$. The reaction mixture was stirred for 30 min and the solvent was removed in vacuo. The residue was triturated with 5 ml of hexane and filtered. The solid was then washed with hexane until the filtrate was colorless and dried under vacuum to give 360.5 mg (93%) of (1) as a brown powder. IR (CH$_2$Cl$_2$) 2955, 1611, 1593, 1545, 1416, 1389, 1198, 841 cm$^{-1}$. Anal. Calcd. for $C_{36}H_{38}F_6MnN_2O_2P$• (H$_2$O) 1.5•(CH$_3$CN) 0.5: C, 56.93; H, 5.30; N, 4.57. Found: C, 57.11; H, 5.50; N, 4.50.

Preparation of:

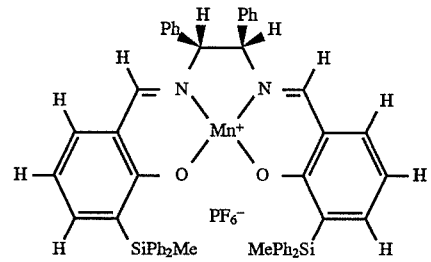

The salicylaldehyde derivative (4) was prepared by the following sequence using well-established procedures in each step:

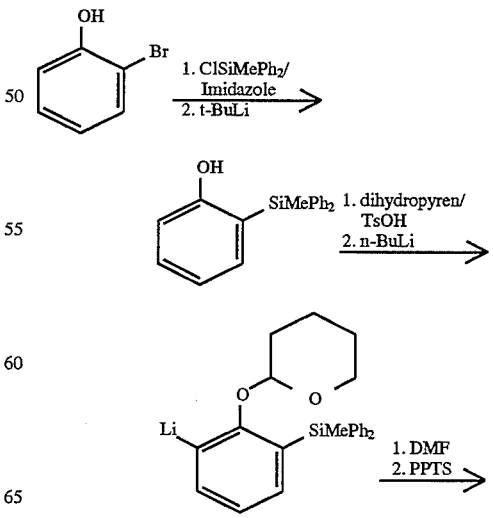

-continued

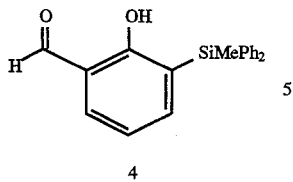

4

(R,R)-1,2-Diphenyl-1,2-bis(3-diphenylmethylsilylsalicylideamino)ethane (5)

A solution of 348.3 mg (1.09 mmol) of (4) and 116.0 mg (0.546 mmol) of (R,R)-1,2-diamino-1,2-diphenylethane in 5 ml of ethanol was heated to reflux for 0.5 h. A bright yellow oil separated from the solution and it solidified upon standing. The mixture was filtered and the yellow solid was washed with 2×5 ml ethanol. The isolated yield of product pure by $^1$H NMR analysis was 416 mg (97%). $^1$H NMR (CDCl$_3$) 80.95 (s, 3H), 4.68 (s, 2H), 6.72–7.55 (m, 36H, ArH), 8.37 (s, 2H), 13.34 (s, 2H) ppm.

((R,R)-1,2-Diphenyl-1,2-bis(3-diphenylmethylsilylsalicylideamino)ethane)manganese(III) Complex (6)

Under strictly air-free conditions, a solution of 32.0 mg (0.48 mmol) of KOH in 2 ml of ethanol was added dropwise to a suspension of 195 mg (0.24 mmol) of (5) in 3 ml of ethanol with stirring. The heterogeneous mixture was stirred for 20 min, and a solution of 51.5 mg (0.24 mmol) of Mn(OAc)$_2$•4H$_2$O in 3 ml of MeOH was then added rapidly. The yellow-orange mixture was stirred for 8 hr. at room temperature, then refluxed under N$_2$ for 4 hr. The solvent was removed in vacuo and the residue was washed with 5 ml of methanol, 5 ml of ethanol, and isolated by filtration. The yield of orange product was 188 mg (90%). This material was used in the next step without any further purification or analysis.

((R,R)-1,2-Diphenyl-1,2-bis(3-diphenylmethylsilylsalicylideamino)ethane)manganese(III) Hexafluorophosphate ((R,R)-1(7)

A solution of 72 mg (0.217 mmol) of ferrocenium hexafluorophosphate in 2 ml of CH$_3$CN was added dropwise to a solution of 188 mg (0.217 mml) of (6) in 3 ml of CH$_3$CN under N$_2$. The reaction mixture was stirred for 30 min and the solvent was removed in vacuo. The solid residue was then washed with hexane until the filtrate was colorless. The brown powder was dried under vacuum to give 201.3 mg (92%) of (7). Anal. Calcd. for C$_{54}$H$_{46}$F$_6$MnN$_2$O$_2$PSi$_2$•(CH$_3$CN) 1.5•(H$_2$O): C, 62.77; H, 4.85; N, 4.50. Found: C, 62.89; H, 4.47; N, 4.57.

Preparation of:

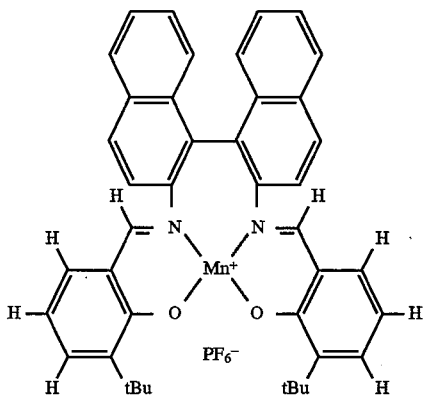

2,2'-Bis(3-tert-Butylsalicylideamino)-1,1'-Binaphthyl

A solution of 725 mg (4.0 mmol) of 3-tert-butylsalicylaldehyde in 6 ml of EtOH was added dropwise to a solution of 569 mg (2.0 mmol) of (+)-2,2'-diamino-1,1'-binaphthyl in 5 ml of EtOH. The reaction mixture was heated to reflux for 8 h and, then volatile materials were removed under vacuum. The residue was purified by flash chromatography on 80 g SiO$_2$, using 20% CH$_2$Cl$_2$ in hexane as eluent. The mobile yellow fraction was collected and solvents were removed under vacuum to give 725 mg (1.20 mmol, 59% yield) of the dimine as a yellow powder.

1,1'-Binaphthyl-2,2'-bis(3-tert-Butylsalicylideamino)-manganese(II) Complex

Under strictly air-free conditions, a solution of 2 mmol of KOH in 2 ml of MeOH is added dropwise to a solution of 1 mmol of 2,2'-bis(3-tert-butylsalicylideamino)-1,1'-binaphthyl in 5 ml of EtOH with stirring under an atmosphere of nitrogen. A solution of 1 mmol of Mn(OAc)$_2$•4H$_2$O in 3 ml of MeOH is added rapidly and the orange mixture is stirred for 24 hr. The solvent is removed in vacuo and the residue was stirred with 5 ml of benzene and filtered to remove KOAc. The filtrate is concentrated to dryness to afford the Mn(II) complex as an orange powder.

1,1'-Binaphthyl-2,2'-bis (3-tert-Butyisalicylideamino)-manganese(III) Hexafluorophosphate A solution of 165.5 mg (0.5 mmol) of ferrocenium hexafluorophosphate in 2 ml of CH$_3$CN is added dropwise to a solution of 0.05 mmol of 1,1'-binaphthyl-2,2'-bis(3-tert-butylsalicylideamino)-manganese(II) complex in 3 ml of CH$_3$CN under N$_2$. The reaction mixture is stirred for 30 min and the solvent is removed in vacuo. The residue is triturated with 5 ml of hexane and filtered. The solid is then washed with hexane until the filtrate is colorless and dried under vacuum to give the Mn(III) salt as a deep green powder.

Preparation of:

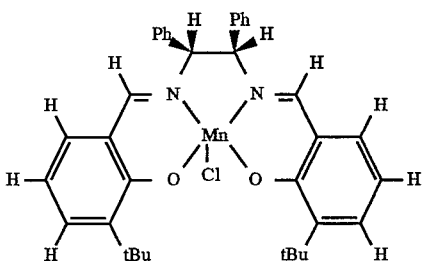

No precautions to exclude air or moisture were necessary in this procedure. A solution of 360.5 mg (2.0 mmol) of 3-tert-butylsalicylaldehyde in 3 ml of absolute ethanol was added dropwise to a solution of 212.3 mg (1.0 mmol) of (R,R)-1,2-diamino-1,2-diphenylethane in 5 ml of ethanol. The reaction mixture was heated to reflux for 1 h and then 245.1 mg (1.0 mmol) of Mn(OAc)$_2$•4H$_2$O was added in one portion to the hot (60° C.) solution. Upon addition, the color of the solution immediately turned from yellow to brown. It was refluxed for an additional 30 min and then cooled to room temperature. A solution of 10% NaCl (5 ml) was then added dropwise and the mixture stirred for 0.5 h. The solvent was then removed in vacuo and the residue was triturated with 50 ml of CH$_2$Cl$_2$ and 50 ml of H$_2$O. The organic layer was separated and the brown solution was washed with saturated NaCl. Separation of the organic phase and removal of solvent afforded crude material which was recrystallized from C$_6$H$_6$/C$_6$H$_{14}$ to give 591 mg (0.938 mmol) of the chloride salt of (1) (94%). Anal. Calcd. for C$_{36}$H$_{38}$ClMnN$_2$O$_2$•(H$_2$O) 0.5: C, 68.63; H, 6.24; N, 4.45. Found: C, 69.01; H, 6.26; N, 4.38.

Procedure for the preparation of the most preferred catalyst of the fourth aspect of the invention (R,R)- and (S,S)-1,2,-bis(3,5-di-tert-butylsalicylide-amino) cyclohexane

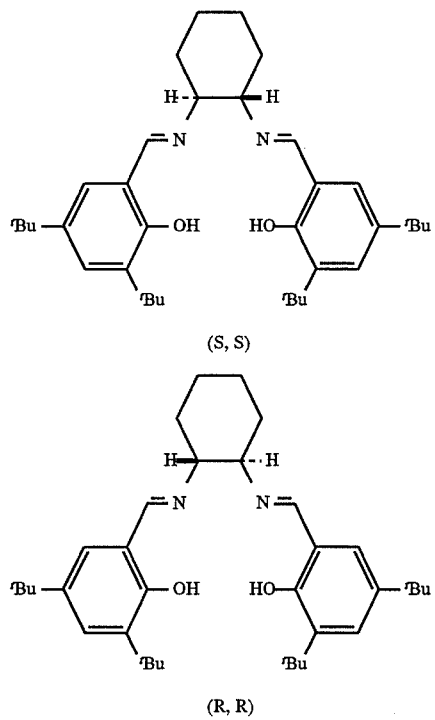

(S, S)

(R, R)

3,5-Di-t-butylsalicylaldehyde (2.0 equivalents) was added as a solid to a 0.2M solution of (R,R) or (S,S) 1,2-diaminocyclohexane (1.0 equivalent) in absolute ethanol. The mixture was heated to reflux for 1 hr. and then H$_2$O was added dropwise to the cooled bright yellow solution. The resulting yellow crystalline solid was collected by filtration and washed with a small portion of 95% ethanol. The yield of analytically pure salen ligand obtained in this manner was 90–97%.

Spectroscopic and analytical data for the salen ligand: $^1$H NMR (CDCl$_3$) δ 13.72 (s, 1H), 8.30 (S, 1H), 7.30 (d, J=2.3 Hz, 1H), 6.98 (d, J=2.3 Hz, 1H), 3.32 (m, 1H), 2.0–1.8 (m, 2H), 1.8–1.65 (m, 1H), 1.45 (m, 1H), 1.41 (s, 9H), 1.24 (s, 9H). $^{13}$C NMR (CDCl$_3$): δ 165.8, 158.0, 139.8, 136.3, 126.0, 117.8, 72.4, 34.9, 33.0, 31.4, 29.4, 24.3. Anal. Calcd for C$_{36}$H$_{54}$N$_2$O$_2$: C, 79.07; H, 9.95; N, 5.12. Found: C, 79.12; H, 9.97; N, 5.12.

(R,R)- and (S,S)-[1,2-bis(3,5-di-tert-butylsalicylide-amino) cyclohexane]manganese(III) chloride The salen ligand immediately above is redissolved in hot absolute ethanol to give a 0.1M solution. Solid Mn(OAc)$_2$•4H$_2$O (2.5 equivalents) is added in one portion and the solution is refluxed for 1 hr. Approximately 5 equivalents of solid LiCl are then added and the mixture is heated to reflux for an additional 0.5 hr. Cooling the mixture to 0° C. and addition of a volume of water equal to the volume of the brown ethanolic solution to afford the Mn(III) complex as a dark brown powder which are washed thoroughly with H$_2$O, and isolated by filtration in, 81–93% yield. Acceptable C, H, N, Cl, and Mn analyses of the catalyst have been obtained (±0.4%), but these vary according to the extent of water and ethanol incorporation in the powdery product. Enantioselectivities in the epoxidation reactions are invariant with different batches of a given catalyst, indicating that the solvent content of the catalyst does not influence its effectiveness.

Analytical data for this catalyst: Anal. Calcd for C$_{36}$H$_{52}$ClMnN$_2$O$_2$•C$_2$H$_5$OH: C, 67.19; H, 8.31; Cl, 5.22; Mn, 8.09; N, 4.12: Observed: C, 67.05; H, 8.34; Cl, 5.48; Mn, 8.31; N, 4.28.

Procedures for the Asymmetric Epoxidation of Chromene Derivatives

Method A (NaOCl as oxygen atom source)

A solution of 0.05M Na$_2$B$_4$O$_7$•10H$_2$O (1.0 ml) was added to a 2.5 ml solution of undiluted commercial household bleach (Clorox®). The pH of the resulting buffered solution was approximately 9.5, and it was adjusted to a pH of 10.5 by addition of a few drops of 1M NaOH solution. To this solution was added a solution of about 0.005 to 0.02 mmol of the catalyst and about 1.0 mmol of olefin in 2.0 ml of CH$_2$Cl$_2$. The two-phase mixture was stirred at room temperature and the reaction progress was monitored by capillary gas chromatography. Reactions were complete within approximately 1–5 hours. After the reaction was complete, 10 ml of CH$_2$Cl$_2$ was added to the mixture and the brown organic phase was separated, washed twice with 10 ml H$_2$O and once with 10 ml saturated NaCl solution, and then dried for 15 min over anhydrous Na$_2$SO$_4$. The solution was faltered and solvent was removed under vacuum. The residue was purified by standard procedures using flash chromatography on 10·g of silica gel using a mixture of CH$_2$Cl$_2$/hexane as the eluting solvent. Pure epoxide was isolated by combination of the product-containing fractions and removal of solvent under vacuum. Enantiomeric excesses were determined by $^1$H NMR using Eu(hfc)$_3$ as a chiral shift reagent, or in the case of stilbene oxide by direct separation by HPLC on a commercial (Regis) covalently-bound leucine Pirkle column. Absolute configurations were assigned by comparison of [α]D with accepted literature values.

Method B (iodosylmesitylene as oxygen atom source)

A solution of 1.0 mmol of olefin, 8 ml CH$_2$Cl$_2$ and 0.04–0.08 mmol of the catalyst was stirred at room temperature as solid iodosomesitylene was added in 0.3 mmol portions at 15–30 minute intervals. Disappearance of starting olefin was complete after addition of 4–10 portions (1.2 to 3 equivalents) of total iodosylmesitylene. Solvent was removed in vacuo, the residue was extracted with hexane, and the mixture was filtered through Celite diatomaceous earth to remove catalyst and other solids. Pure epoxide was obtained by flash chromatography (10 g SiO$_2$, CH$_2$Cl$_2$/hexane eluent). The optical purity of this material was determined by the method described above.

Asymmetric Epoxidation of Representative Olefins with the most preferred embodiment of the first aspect

Examples 1–7

| Entry | Olefin[a] Catalyst | Yield[b] (%) | ee (%) | Config-uration[c] | Method |
|---|---|---|---|---|---|
| 1 | (R,R)-1 | 50 | 59 | 1R,2S-() | B |
| 2 | (R,R)-1d | 75 | 57 | R-(+) | A |
| 3 | (R,R)-1d | 72 | 67 | (+)e | B |
| 4 | (R,R)-1 | 52 | 93 | (−)e | B |
| 5 | (R,R)-1 | 70 | 85 | 1R,2S-(−) | A |
| 6 | (R,R)-1[d] | 72 | 78 | 1R,2S-(+) | B |
| 7 | (R,R)-1 | 36 | 30 | R-(+) | B |

[a]Reactions were run at 25° C. unless otherwise noted.
[b]Isolated yields based on olefin.
[c]The sign corresponds to that of $[\alpha]_D$.
[d]Reaction run at 5° C.
[e]Absolute configuration not known.

The table above shows that the highest enantiomeric excess (ee) values were observed with Examples 4, 5, and 6, i.e. cis disubstituted olefins. In contrast, Example 7, a 1,1 disubstituted olefin, had the lowest ee values. Example 1, a trans disubstituted olefin, and Examples 2 and 3, monosubstituted olefins, had intermediate ee values.

Asymmetric Epoxidation of Representative Olefins with Catalysts from the first and fourth aspects of the invention

Examples 8–16

Figure 11:
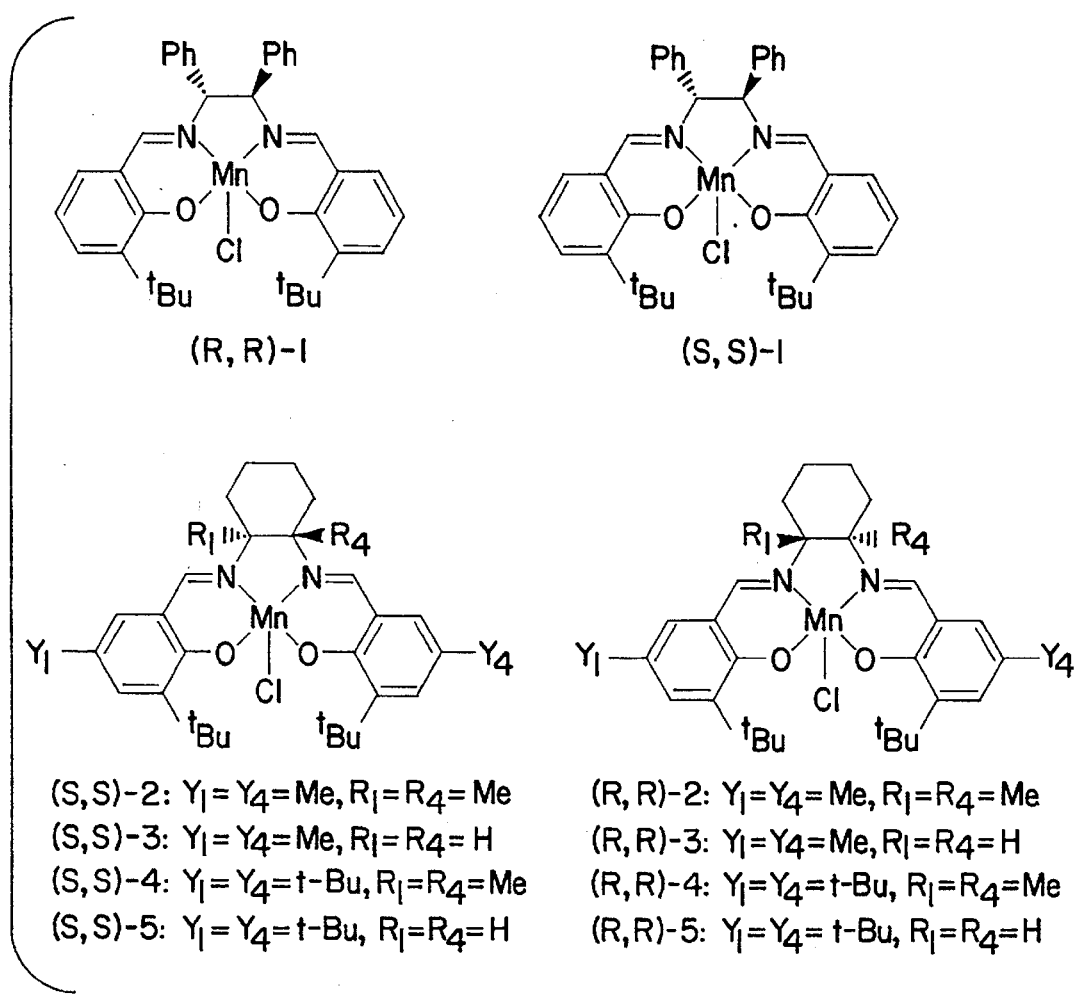
FIG. 11 shows 2-dimensional structures for various embodiments of the present invention with the numbering system used in Examples 8–16.
Figure 12:
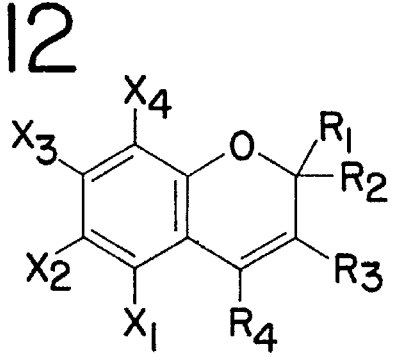
FIG. 12 shows the structure of the chromene derivatives used in the present method.

The following Examples 8–16 were run the same as Examples 17, except that different catalysts were used. The key to the catalyst numbering system is found in FIG. 11. As can be seen, Example 8 was made according to the most preferred embodiment of the first aspect. Examples 9–16 were made according to the fourth aspect, with the catalyst used in Examples 12–16 being the most preferred embodiment of the fourth aspect. It is also noted that all of Examples 8–16 were run with method B described above.

TABLE II $$R\diagup\!\!=\!\!\diagdown R' \xrightarrow[CH_2Cl_2]{\text{catalyst (3–10 mol\%)}} R\diagup\!\!\triangle\!\!\diagdown R' \text{ (O)}$$
(NaOCl)

| Entry | Olefin[a] | Catalyst | Yield[b] (%) | ee[c] (%) | Configuration[d] |
|---|---|---|---|---|---|
| 8 | Ph―CH=CH―CH₃ (cis) | (R,R)-1 | 70 | 85 | 1R,2S-(−) |
| 9 | | (S,S)-2 | 75 | 49 | 1S,2R-(+) |
| 10 | | (S,S)-3 | | 80 | 1S,2R-(+) |
| 11 | | (S,S)-4 | | 55 | 1S,2R-(+) |
| 12 | | (S,S)-5 | 82 | 92 | 1S,2R-(+) |
| 13 | 4-Cl-C₆H₄-CH=CH-CH₃ (cis) | (S,S)-5 | 74 | 94 | |
| 14 | 2-(C(CH₃)₂-O)-C₆H₄-CH=CH (cis) | (S,S)-5 | 87 | 97 | n.d. |
| 15 | cyclohexyl ketal olefin | (S,S)-5 | 53 | 94 | R,R-(+) |
| 16 | Ph-CH=CH-CO₂Me | (S,S)-5 | 74 | 75 | S,S-(−) |

[a]Reactions were run at 0° C.
[b]Isolated yields based on olefin.
[c]Determined by $^1$H NMR analysis in the presence of Eu(hfc)$_3$ and by capillary GC using a commercial shiral colum (J & W Scientific Cyclodex-B column, 30 m × 0.25 mm I.D., 0.25 µm film).
[d]All reactions were run in duplicate with both enantiomers of each catalyst. Reactions carried out with (R,R)-5 afforded epoxides with absolute configurations opposite to those in the table and with the same ee's (± 2%). The sign corresponds to that of $[\alpha]_D$.

As shown in Examples 12–15, the most preferred catalyst of the fourth embodiment catalyzes the epoxidation of cis-disubstituted olefins with excellent enantioselectivity.

Examples 17–24

Epoxidation of Chromene Derivatives

The following Examples 17–24 were carried out to show the effectiveness of the present method to enantioselectively epoxidize various chromene derivatives. The catalyst used in these examples is the R,R enantiomer shown in FIG. 8. The method described above as Method A was used for these examples:

The results are shown in Table III. It is noted that the unsubstituted chromene in Example 24 did not produce an epoxychroman.

TABLE III

| Example No. | Olefin | Major Product(s) | ee (%)[b] | Isolated Yield (%)[c] | Absolute Configuration |
|---|---|---|---|---|---|
| 17 | [structure: 6-cyanochromene] | [structure: epoxide] | 97 | 96 | (3R,4R)-(+)[d] |
| 18 | [structure: 6-nitrochromene] | [structure: epoxide] | 94 | 76 | (3R,4R)-(+)[e] |
| 19 | [structure: chromene] | [structure: epoxide] | 96 | 97 | (3R,4R)-(+)[e] |
| 20 | [structure: acetyl-methoxy chromene] | [structure: epoxide] | 98[f] | 75 | (3R,4R)-(+)[e] |
| 21 | [structure: methyl chromene] | [structure: epoxide] | 97[f] | 51 | (3R,4R)-(+)[e] |
| 22 | [structure: cyanochromene] | [structure: epoxide] | >96 | 82 | (3R,4R)-(+)[g] |
| 23 | [structure: naphthochromene] | [structure: diol] 18:tran/cis = 2:1 | trans:94[f] cis: 95[f] | 38[h] | not determined |
| 24 | [structure: chromene] | [structure: lactone] | — | 49 | |

[a] Epoxidations carried out with (S,S)-4 afforded products of opposite configuration.
[b] Ee's were determined by GC (see caption to FIG. 1) unless otherwise noted.
[c] Isolated yield correspond to reactions carried out on 1 mmol scale with 4 mol % 4 and product isolation by flash chromatography.
[d] Correlated with (3R,4S)-(+)-2 (ref. 9b).
[e] Absolute configuration assigned by analogy to 6.

TABLE III-continued

| Example No. | Olefin | Major Product(s) | ee (%)[b] | Isolated Yield (%)[c] | Absolute Configuration |
|---|---|---|---|---|---|

[f]Ee determined by $^1$H NMR using Eu(hfc)$_3$ as chiral shift reagent.
[g]Personal communication from Drs. R. Gericke and J. Sombroek (E. Merck).
[h]Isolated yield of the 2:1 mixture.

Example 25

Example 25 was carried out the same as Example 19 above, with the exception that the catalyst shown in FIG. 2 was used. The isolated yield was found to be 78% and the ee was 91%.

Example 26

Example 26 was carried out as a larger scale production of the epoxychroman produced in Example 17 above, namely 6-cyano-2,2-dimethyl-3,4-epoxychroman.

The pH of a solution of commercial household bleach (Clorox®) was buffered to pH=11.3 with 0.05M Na$_2$HPO$_4$ and 1N NaOH and then cooled, to 0° C. To 500 ml of this solution (approximately 0.55M in NaOCl) was added a 0° C. solution of 6-cyano-2,2-dimethylchromene and the catalyst (3.1 g, 5.0 mmol, 3.7 mol %) in 135 ml of CH$_2$Cl$_2$. The two-phase system was mechanically stirred at 0° C. and the reaction progress was monitored by HPLC. After 9 hours, the heterogeneous brown mixture was filtered through a pad of Celite diatomaceous earth and the organic phase was separated, washed once with 500 ml saturated NaCl solution, and then dried (Na$_2$SO$_4$). The ee of the crude product obtained after solvent removal was determined for each example by GC analysis. The brown oily residue was then dissolved in 200 ml of boiling absolute ethanol and then water (200 ml) was added slowly to the hot solution. A hot gravity filtration afforded a pale yellow solution from which the crystallized epoxychroman was isolated. This isolated yield was 81% and the ee was measured at 99% by GC analysis.

Example 27

Figure 13:
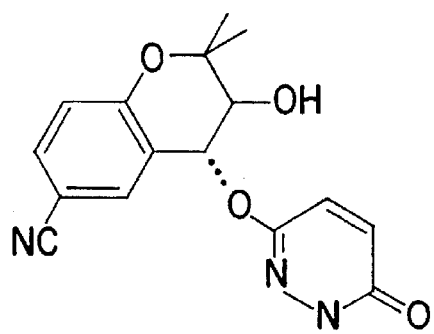
FIG. 13 shows the structure of the 3S, 4R enantiomer of one cromakalim compound.

Example 27 was carried out to produce the cromakalin compound shown in FIG. 13. The epoxychroman produced in Example 26, namely 6-cyano-2,2-dimethy-3,4-epoxyehroman, (1 g, 4.97 mmol), 3-hydroxy-1-methyl-1,6-dihydropyridazin-6-one (0.652 g, 5.17 mmol) and pyridine (0.491 g, 6.21 mmol) were refluxed together in ethanol (10 ml) for 8 hours. The homogenous yellow mixture was then concentrated under vacuum and the residue was isolated by flash chromatography on 70 g of silica and ethyl acetate as eluent. The isolated yield was 1.38 g (85%).

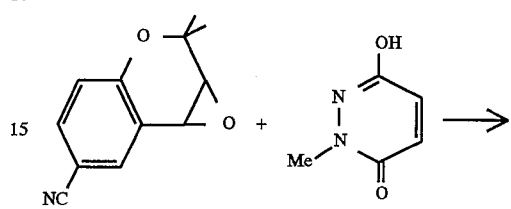

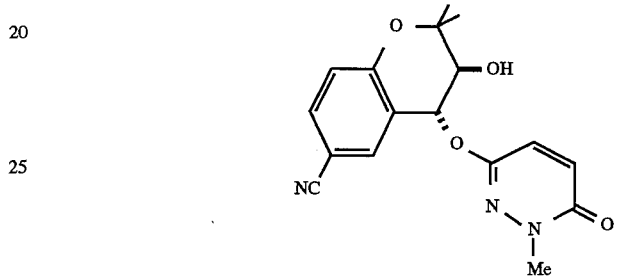

Example 28

Figure 14:
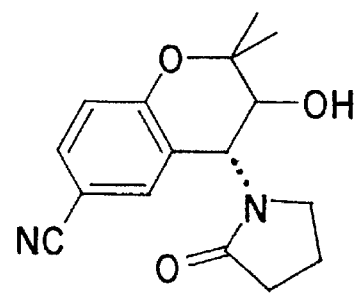
FIG. 14 shows the structure of the 3S, 4R enantiomer of another cromakalim compound.
Figure 15:
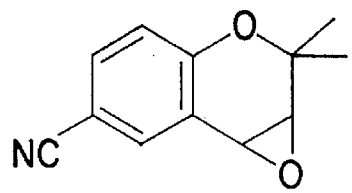
FIG. 15 shows the structure of 6-cyano-2,2-dimethyl-3, 4-epoxychroman.
Figure 16:
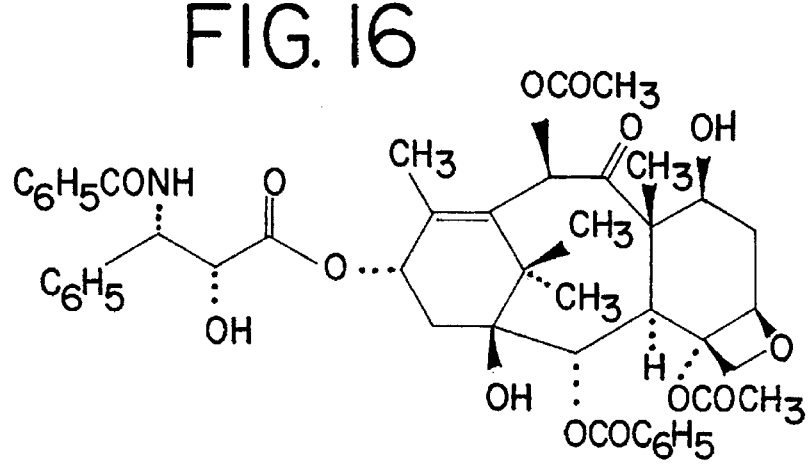
FIG. 16 shows the structure of taxol.
Figure 17:
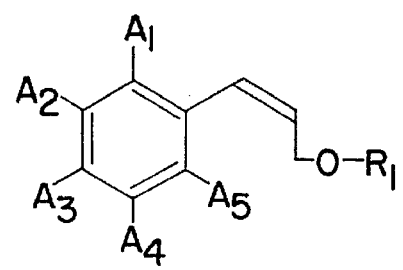
FIG. 17 shows the structure of the cinnamate derivatives used in the present method.
Figure 18:
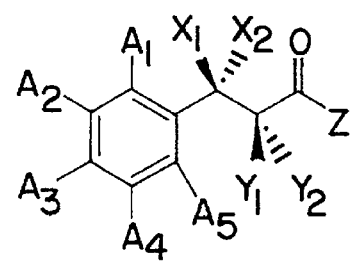
FIG. 18 shows the generalized structure and analogs of the 3S, 4R enantiomer of the C-13 side chain of taxol.

Example 28 was carded out to produce the cromakalin shown in FIG. 14. Sodium hydride (0.199 g of a 60% suspension in mineral oil, 4.97 mmol) was suspended in DMSO (1.5 ml) and 2-pyrrolidinone (0.423 g, 4.97 mmol) was added to the stirred mixture at room temperature under a dry nitrogen atmosphere. The epoxychroman from Example 26 (1 g, 4.97 mmol) was then added as a solid to the grey foamy mass. The mixture was stirred at room temperature for 10 hours. The orange-red mixture was then treated with 10 ml of water and the resulting thick yellow precipitated was extracted 5 times with 10 ml of ethyl acetate. Removal of solvent and chromatography on silica (100 g, ethyl acetate eluent) afforded pure product which was recrystallized from ethyl acetate. This isolated yield was 0.808 g (56%).

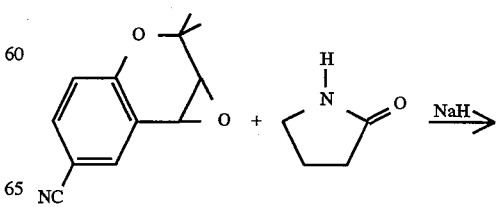

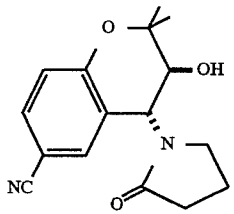

Synthesis of Taxol and Taxol Intermediates and Analogs

The following general comments apply to the following examples. Melting points were obtained in open capillary tubes with a Laboratory Devices (Holliston Mass.) Mel-Temp II melting point apparatus and are reported uncorrected. The boiling points are reported uncorrected. The $^1$H NMR spectra were obtained on a General Electric (Schenectady N.Y. QE-300 (300 MHz) spectrometer. Low resolution EI gas chromatography/mass spectroscopic (GC/MS) analyses were performed on a Hewlett-Packard (Palo Alto Calif.) 5970 Mass Selective Detector coupled to a Hewlett-Packard 5890 gas chromatograph. Other mass spectra were provided by the Mass Spectrometry Laboratory at the University of Illinois, Urbana, Ill. Elemental analyses were performed by the Microanalytical Laboratory of the University of Illinois.

Silica gel chromatographic purifications were performed by flash chromatography with Woelm silica (Aldrich Chemical Co., Milwaukee Wis.) packed in 32–64 m glass columns. The weight of silica gel was approximately 50–100 times that of the sample unless it is noted otherwise below. The eluting solvent for each purification was determined by thin layer chromatography (TLC). Analytical TLC was conducted on Merck glass plates coated with 0.25 mm of silica gel 60 F$_{254}$. TLC plates were visualized with ultraviolet light and/or in an iodine chamber unless noted otherwise. Gas-liquid chromatographic (GC) analyses were performed on a Hewlett-Packard HP 5890 gas chromatograph using the following columns: A) J&W Scientific (Folsom Calif.) 0.32 mm×30 m DB-5 capillary column or B) J&W Scientific CPX-B (β-cyclodextrin) capillary column, 30 m. Optical rotations were measured on a Jasco (Japan Spectrophotometric Co., Tokyo, Japan) Dip-360 digital polarimeter.

The buffered bleach solutions employed in the epoxidation reactions were prepared from Clorox® bleach according to the method of Zhang W.; and Jacobsen, EN: J. Org. Chem. 56: 2296, 1991. Unless other noted, all starting materials were purchased from Aldrich and were used as received.

Example 29

Preparation of Methyl 3-Phenylglycidate

A quantity of cis-methyl cinnamate (4.5 mg, 2.5 mmol) was dissolved in 6 ml of CH$_2$Cl$_2$. 3,5-Dimethylpyridine-N-oxide (125 mg, 40 mol %) was then added to the solution, followed by the addition of catalyst (S,S)-4 (150 mg, 10 mol %). The resulting solution was cooled to 0° C. and combined with bleach solution (15 ml at a pit of 11.25) pre-cooled to 4° C. The reaction mixture was stirred at 4° C. for three hours. Hexane (60 ml) was then added to the reaction mixture. The organic phase was washed once with 30 ml water and twice with 3 ml brine and dried over Na$_2$SO$_4$. Solvent was removed under vacuum and the residue-was purified by chromatography (EtOAc/hexane=7:93, v/v) to provide an inseparable mixture of cis- and trans-methyl-3-phenylglycidate in which the cis:trans ratio was 4:1. The yield was 356 mg, or 80%. The assignment of stereoisomers and determination of ratio of stereoisomers was based on the literature values for $^1$H NMR of cis-methyl-3-phenylglycidate. Denis, J. N.; Greene, A. E.; Serra, A. A.; Luche, M.-J.: J. Org. Chem. 51: 46, 1986. The ee's of the cis- and trans-epoxides were determined to be 87–89% and 60%, respectively, by GC analysis (using column B described above).

Example 30

Preparation of cis-Ethyl Cinnamate

Ethyl phenylpropiolate (10.8 g, 0.062 mol) was dissolved in hexane (540 ml), followed by addition of quinoline (11.2 g) and palladium on calcium carbonate (Lindlax catalyst, 3.6 g). The resulting reaction mixture was stirred under hydrogen (1 atm) at room temperature, and the progress of the reaction was monitored closely by GC analysis. The reaction was stopped by displacement of the hydrogen atmosphere with nitrogen once the rate of absorption of hydrogen was observed to decrease abruptly. The resulting mixture was filtered through a pad of diatomaceous earth and the filtrate was dried over Na$_2$SO$_4$. Solvent was removed under reduced pressure. Then the residue was distilled under vacuum (2.5 mm Hg, at 98°–100° C.) to provide 10.08 g of cis-ethyl cinnamate, for a yield of nearly 95%. By GC analysis, this product mixture was found to contain 5.7% over-reduced alkane and 3.5% trans-ethyl cinnamate, but was used without further purification.

Example 31

Preparation of (2R,3R)-Ethyl-3-Phenylglycidate

With 1.76 g or 10 mmol of cis-ethyl cinnamate prepared as described in Example 30, 4-phenylpyridine-N-oxide (420 mg, 2.5 mmol) was dissolved in CH$_2$Cl$_2$(20 ml). Catalyst (the R,R-enantiomer of FIG. 8) (360 mg, 0.6 mmol) was added to the solution. This solution and the buffered bleach solution (25 ml, at pH=11.25) were cooled separately in ice bath, and then combined at 4° C. The two-phase mixture was stirred for two hours, or until the disappearance of cis-ethyl cinnamate was judged to be complete by TLC analysis. Ethyl acetate (200 ml) was then added to the solution and the organic phase was separated, washed with water (2×100 ml) and brine (1×100 ml). Then the organic phase was dried over Na$_2$SO$_4$. The solvent was removed under vacuum and the residue was subjected to GC analysis, which indicated the presence of cis- and trans-epoxides in a 3:1 ratio. The residue was distilled (2 mm Hg, at 75°–77° C.) to provide 1.6 g (80% yield) of a crude mixture of 75% cis-epoxide, 18% trans-epoxide and several minor impurities, as determined by GC analysis. The ee of the cis-epoxide was determined to be 96–97% by a $^1$H NMR shift study with Eu(hfc)$_3$ as chiral shift reagent. The ee of the trans-epoxide was measured to be 78% by the same method. The mixture was used in subsequent reactions without further purification. The following was obtained for cis-ethyl-3-phenylglycidate: $^1$H NMR (CDCl$_3$) δ 1.02 (t, J=7.2 Hz, 3H), 3.83 (d, J=4.8 Hz, 1H), 3.9–4.1 (m, 2H), 4.27 (d, J=4.8 Hz, 1H), 7.2–7.5 (aromatic, 5H). The following was obtained for trans-ethyl-3-phenlyglycidate: $^1$H NMR (CDCl$_3$) δ 1.33 (t, J=7.2 Hz, 3H), 3.51 (d, J=2.1 Hz, 1H), 4.09 (d, J=1.8 Hz, 1H), 4.2–4.4 (m, 2H), 7.2–7.5 (aromatic, 5H).

Example 32

Preparation of (2R, 3S)-3-Phenyl-Isoserinamide

First, 900 mg, or 4.22 mmol, of (2R, 3R)-3-phenylglycidate, prepared as described in Example 31, was dissolved in a solution of 20 ml of ethanol saturated with ammonia (prepared by passing ammonia through ethanol at −15° C. for 15 minutes). This solution was placed in an autoclave and heated to 100° C. for 16 hours with external agitation. After the solution was cooled to more temperature, agitation was continued for another eight hours. Solvent was removed under vacuum and the residue was recrystallized from ethanol. White crystalline product, weighing 540 mg, was isolated by filtration for a yield of 71%. The melting point was 172°–173° C. The following $^1$H NMR (DMSO-d$_6$/D$_2$O) data were obtained for this compound: δ 3.87 (d, J=3.3 Hz, 1H), 4.08 (d, J=3.3 Hz, 1H), 7.0–7.5 (aromatic, 5H). Analytical for C$_9$H$_{12}$O$_2$N$_2$: Calculated: C, 60.00; H, 6.67; N, 15.55. Found: C, 59.90; H, 6.71; N, 15.25.

The corresponding racemate was synthesized by an analogous sequence with epoxide prepared with the (S,S) catalyst of FIG. 8. The melting point for the racemate was 192°–193° C., which compared favorably to the literature value of 187°–188° C. Kamandi, E.; Frahm, A. W.; and Zymalzowski, F.: Arch. Parmaz. 307: 871, 1974.

Example 33

(2R, 3S)-3-Phenyl-Isoserine (2R,3S)-3-phenyl-isoserinamide (200 mg, 1.11 mmol), as prepared in Example 32, was combined with 354 mg (1.12 mmol) of Ba(OH)$_2$•8H$_2$O and water (2 ml). The resulting suspension was heated to reflux for nine hours. After the reaction mixture was cooled to 80° C., 15 ml of water was added to the solution. The temperature of the solution was maintained at 80° C. for 20 minutes before a solution of 110 mg, 1.11 mmol of concentrated sulfuric acid in 1 ml of water was added. A white precipitate appeared in the solution which was determined to have a pH of between 5 and 7. Heating at 80° C. was maintained for another 20 minutes, and the mixture was then cooled to room temperature. The resulting precipitate (BaSO$_4$) was centrifuged to the bottom of the container, the supernatant was separated, and solvent was removed under vacuum. The resulting white solid was extracted with acetone and collected by filtration to provide 148 mg of the title compound, for a yield of 74%. The material melted with decomposition at 238° C. The $^1$H NMR (D$_2$O/NaOD) data were as follows: δ 3.94 (d, J=3.9 Hz, 1H), 4.01 (d, J=3.9 Hz, 1H), 7.0–7.5 (aromatic, 5H). Analytical for C$_9$H$_{11}$NO$_3$: Calculated: C, 59.66; H, 6.07, N, 7.73. Found: C, 59.10; H, 6.11; N, 7.61.

Example 34

N-Benzoyl-(2R,3S)-3-Phenyl-Isoserine

First, 60 mg (0.33 mmol) of (2R, 3S)-3-phenyl-isoserine, as prepared in Example 33, was dissolved in a 10% aqueous NaHCO$_3$ (8 ml). The solution was cooled to 4° C. and then 143 mg (1.0 mmol) of benzoyl chloride in 120 ml aqueous solution was added. This mixture was stirred for six hours at 4° C. and then acidified to a pH of 1 by addition of dilute HCl solution. The resulting white precipitate was collected by filtration. The volume of the filtrate- was reduced to 2 ml and a second portion of precipitate was collected and combined with the first crop. This material contained both desired product and benzoic acid. The benzoic acid was removed, by stirring for six hours in ether (3 ml) containing several drops of ethanol. Next, 60 mg of the resulting product was isolated as a white solid by filtration, for a yield of 70%. This compound was determined by be more than 95% pure by $^1$H NMR. The melting point was 177°–179° C., compared to a literature value of 167°–169° C. FABMS: m/e 286 (M$^+$+1). The $^1$H NMR (DMSO-d$_6$) values were as follows: δ 4.37 (d, J=4.5 Hz, 1H), 5.46 (dd, J=8.7 Hz and 4.5 Hz, 1H), 5.3–5.7 (b, 1H), 7.2–7.6 (m, 9H), 7.84 (d, J=7.5 Hz, 1H), 8.58 (d, J=9.0 Hz, 1H), 12.5–13.0 (br, 1H). FABHRMS for C$_{16}$H$_{16}$NO$_4$: Calculated: 286.1079. Observed: 286.1068. [α]$^{25}$D−35.9° (c 0.565, EtOH); compared to literature values for the (2S,3R)-isomer of [α]$^{25}$D−36.5° (c 1.45, EtOH) and for the (2R,3S)-isomer of [α]$^{25}$D−37.78° (c 0.9, EtOH). Ojima I., et at. J. Org. Chem. 56: 1681, 1991.

Example 35

Taxol

The N-benzoyl-(2R,3S)-3-phenyl-isoserine, as prepared in Example 34, is treated with 1-chloroethyl ethyl-ether in the presence of a tertiary amine to produce optically pure (2R,3S)-N-benzoyl-O-(1-ethoxyethyl)-3-phenyl-isoserine (2). 7-tri-ethylsilyl baccatin III (1), as synthesized according to Denis et at. (J. Amer. Chem. Soc. 110:5417, 1988), is added to 6 equiv of optically pure (2R,3S)-N-benzoyl-O-(1-ethoxyethyl)-3-phenyl-isoserine (2), 6 equiv of di-2-pyridyl carbonate (DPC), and 2 equiv of 4-(dimethylamino) pyridine (DMAP) in toluene solution (0.02M). This mixture reacts at 73° C. for 100 hours to produce the C-2', C-7-protected taxol derivative (3).

Concomitant removal of the protecting groups at C-2' and C-7 in (3) is accomplished with 0.5% HCl in ethanol at 0° C. for 30 hours to produce taxol, whose identity and purity are established via comparison with the melting point, rotation, and spectral (IR, MNR, FABMS) and chromatogmphic (TLC, HPLC) characteristics of the natural product.

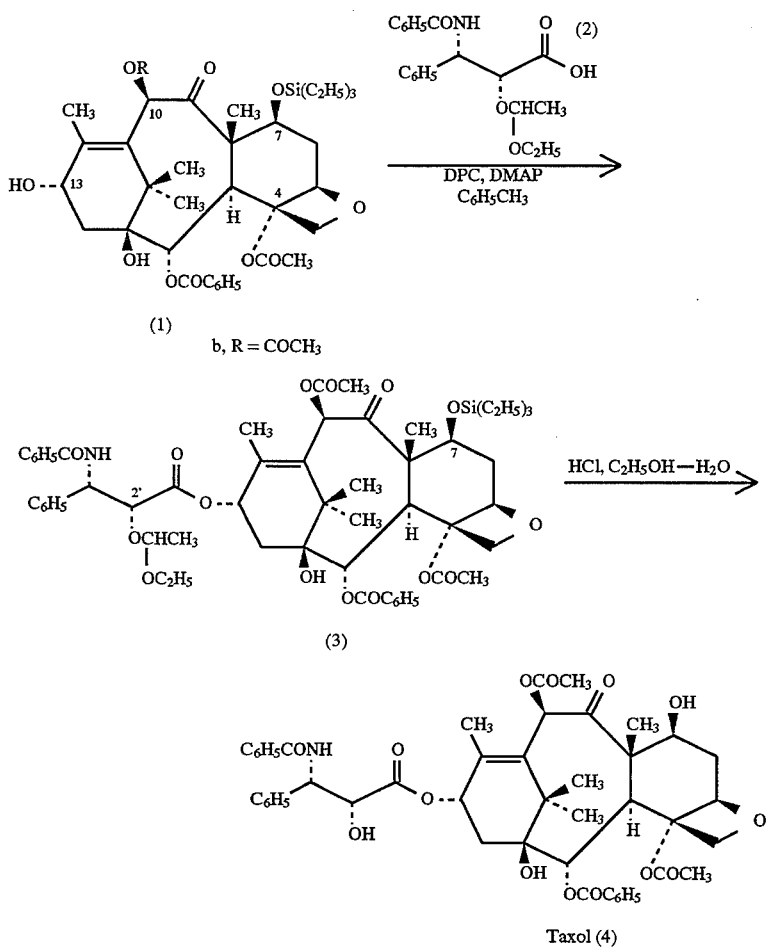

Taxol (4)

Examples 36–39

Effect Of Pyridine-N-Oxide Derivative on Epoxidation

The four alkenes shown in Table IV below were epoxidized with the presence of a pyridine-N-oxide derivative in the following manner.

A solution of 10 mmol of an alkene and 2.0 mmol (20 mol %) of a pyridine-N-oxide derivative were dissolved in 10 ml of $CH_2Cl_2$. Either 4-phenylpyridine-N-oxide (A in the table) or 4-t-butylpyridine-N-oxide (B in the table) was used.

Then, 0.08–1.0 mmol (0.8–10 mol %) of Catalyst 1 or 2 (see below) were added to the alkene solution. The table shows the amounts of catalyst used in each example. This solution and buffered bleach solution (pH=11.25) were cooled separately in an ice bath and then combined at 0°–4° C. This two-phase mixture was stirred for one to five hours. Then, 200 ml of hexane was added to the solution, and the organic phase was separated and washed once with 100 ml water and once with 100 ml brine. The organic phase was then dried over $Na_2SO_4$. The solvent was removed under vacuum. The residue was subjected to purification distillation but could also be purified by chromatography or crystallization. The enantiomeric compositions of the epoxide were established by GC on a chiral capillary column and by $^1H$ NMR with a chiral shift reagent $(Eu(hfc)_3)$.

| Example No. | Olefin | Major Epoxide Product | Catalyst (mol %) | N-Oxide Derivative | Isolated Yield (%) | ee (%) |
|---|---|---|---|---|---|---|
| 36 | (indene) | (indene oxide) | 1(0.8) | B | 70 | 85 |
| 37 | (dihydronaphthalene) | (dihydronaphthalene oxide) | 1(5) | A | 65 | 88 |
| 38 | (cyclohexene dioxolane) | (epoxide dioxolane) | 2(10) | A | 50 | 93 |
| 39 | (cyclopentene dioxolane) | (epoxide dioxolane) | 2(10) | A | 50 | 93 |

It should be noted that, although much of the discussion has involved the use of salen derivatives (made from ethylenediamines), salpn derivatives (made from propylenediamines) and salbn derivatives (made from butylenediamines) are also within the scope of the present invention. Certainly, these are considered to lie within the scope of the invention as defined by the appended claims.

Asymmetric Oxidation of Sulfides

Example 40

The following catalysts were prepared using the same techniques as previously discussed.

FIGS. 9 and 20, as well as Table V below, show the generalized structures of the catalysts.

TABLE V

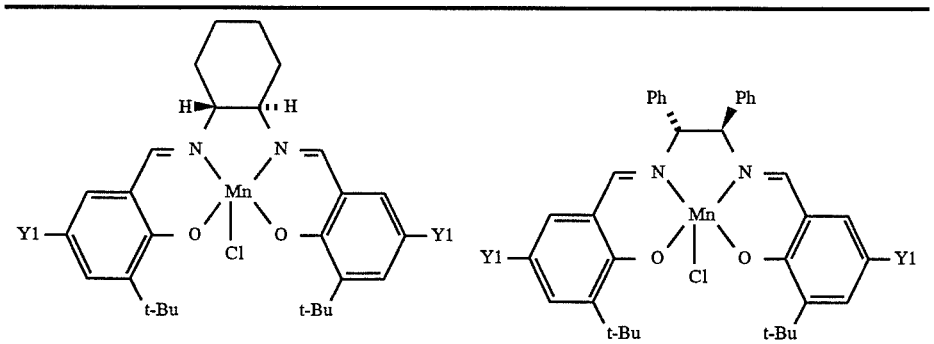

1: Y1 = OMe
2: Y1 = tBu
3: Y1 = NO₂
4: Y1 = H

5: Y1 = OMe
6: Y1 = tBU
7: Y1 = Me

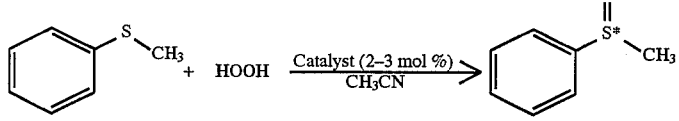

| Entry | Catalyst | Yield, %ª | ee, %ᵇ | Sulfoxide confgnᶜ |
|---|---|---|---|---|
| 1 | (R,R)-1 | 90 | 47 | S-(−) |
| 2 | (R,R)-2 | 72 | 24 | S-(−) |
| 3 | (R,R)-3 | 82 | 0 | — |
| 4 | (R,R)-4 | 74 | 14 | S-(−) |
| 5 | (R,R)-5 | 86 | 36 | S-(−) |
| 6 | (R,R)-6 | 64 | 34 | S-(−) |
| 7 | (R,R)-7 | 84 | 7 | R-(+) |

ªAll yields correpsond to pure products isolated by flash chromatography.
ᵇEe's were determined by HPLC usig a Chiralcel OD column.
ᶜAbsolute configuration assigned by comparison of the sign of $[\alpha]_D$ to the literature value.

These seven catalysts were reacted with thioanisole to measure their ee values. It is significant that those ligand properties that were proven to be important for optimal enantioselectivity in epoxidation were also important in sulfide oxidation. For example, the presence of bulky substituents on the 3,3' and 5,5' positions of the salen ligands has a marked effect on selectivity, indicating that these groups improve sterochemical communication in the transition state leading to oxo transfer by inducing substrate approach near the dissymmetric diimine bridge. An electronic effect on enantioselectively was also, very pronounced in sulfide oxidation with (salen)Mn catalysts. As exhibited in the epoxidation reaction, catalysts bearing electron withdrawing substituents are less enantioselective than electron rich analogs (entries 1, 3 and 4 in Table V). This effect may be attributed to the greater reactivity and concomitant lower selectivity, of the high valence intermediates bearing electron withdrawing groups.

Catalyst 1 of Table V emerged as the most selective of the catalysts tested. Therefore, Catalyst 1 was used to study the asymmetric oxidation of prochiral sulfides. The results of these tests are shown by Table VI below.

Asymmetric Oxidation of Prochiral Sulfides Using Catalyst (R,R)-1 or (S,S)-1.

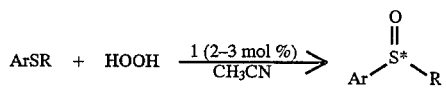

| Entry | Sulfide | Catalyst | Yield (%)ª | ee (%)ᵇ | Sulfoxide confgnᶜ |
|---|---|---|---|---|---|
| 1 | C₆H₅–S–CH₃ | (R,R)-1 | 90 | 47 | S-(−) |
| 2 | o-Br—C₆H₄–S–CH₃ | (R,R)-1 | 80 | 68 | S-(−) |
| 3 | p-CH₃—C₆H₄–S–CH₃ | (R,R)-1 | 95 | 42 | S-(−) |

-continued

Asymmetric Oxidation of Prochiral Sulfides Using Catalyst (R,R)-1 or (S,S)-1.

$$ArSR + HOOH \xrightarrow[CH_3CN]{1\ (2-3\ mol\ \%)} \underset{Ar}{\overset{O}{\underset{\|}{S^*}}}R$$

| Entry | Sulfide | Catalyst | Yield (%)[a] | ee (%)[b] | Sulfoxide confgn[c] |
|---|---|---|---|---|---|
| 4 | C6H5—S—△ | (R,R)-1 | 84 | 40 | S-(−) |
| 5 | C6H5—S—i-C4H8 | (R,R)-1 | 94 | 43 | S-(−) |
| 6 | 2-napthyl—S—CH3 | (R,R)-1 | 84 | 46 | S-(−) |
| 7 | o-MeO—C6H4—S—CH3 | (S,S)-1 | 94 | 34 | R-(+)[d] |
| 8 | p-NO2—C6H4—S—CH3 | (R,R-1 | 86 | 66 | S-(−)[d] |
| 9 | m-NO2—C6H4—S—CH3 | (S,S)-1 | 84 | 63 | R-(+)[d] |
| 10 | p-Br—C6H4—S—CH3 | (S,S)-1 | 93 | 56 | R-(+)[d] |
| 11 | o-I—C6H4—S—CH3 | (S,S)-1 | 95 | 65 | R-(+)[d] |

[a]Isolated yields based on sulfide. Pure sulfoxides (>99% by GC analysis) were isolated by flash chromatography.
[b]Ee's were determined by HPLC using a Chiralcel OD column except for entries 8, 9, 10 which were determined by $^1$H NMR in the presence of (R)-(−)-2,2,2-trifluoro-1-(9-anthryl)ethanol.
[c]Absolute configurations were established by comparison of the sign of $[\alpha]_D$ to literature values unless otherwise indicated.
[d]Absolute configurations assigned by analogy (sign of $[\alpha]_D$) to entries 1–6.

Figure 21:
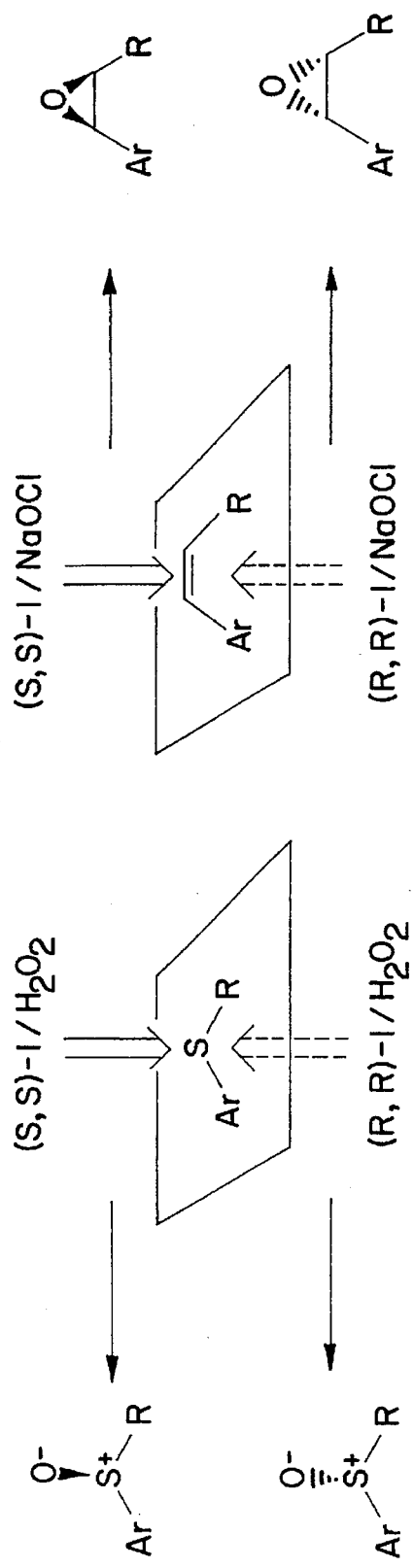
FIG. 21 shows the face selectivity in sulfide oxidation reactions.

Selectivities in these cases were moderate, although a significant electronic effect on substrate could be discerned. More reactive electron rich sulfides were oxidized with lower selectivity (e.g. entry 7, Table VI), while selectivities above 60% ee were obtained with substrates bearing halide or nitro groups (entries 2, 8–11, Table VI). The face selectivity in the sulfide oxidation reactions is analogous to that in the alkene epoxidation (see FIG. 21). This suggests that the nature Of the transition states in the two processes may be similar.

Catalytic Disproportionation of Hydrogen Peroxide

Example 41

Preparation of:

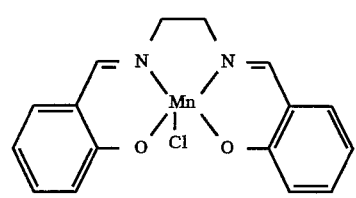

A solution of salicylaldehyde (24.42 g, 0.200 mole) in 80 ml of EtOh was added to a stirred solution of ethylenediamine (6.070 g, 0.100, olc) in a mixture of 50 ml EtOH and 50 ml of H$_2$O over a period of 5 minutes. The reaction mixture was refluxed for 1 hour and stirred at room temperature overnight. The yellow crystalline product was separated by filtration and washed with 2×30 ml of cold 60% EtOh and air dried to yield 25.733 g (95.9%) of salen.

Mn(OAc)2 (24.509 g, 0.100 mole) was added to a stirred solution of 13.416 g of salen in 1000 ml of 95% EtOH and the color immediately changed from yellow to dark brown. The resulting mixture was refluxed for 3 hours. The solvent was removed by vacuum and the resulting residue was extracted with 1250 ml of hot water (60 degrees C.) and filtered. Solid NaCl (58.44 g, 1.000 mole) was added to the filtrate and brown precipitate formed immediately. The precipitate was collected by filtration and dried. The crude product was recrystallized from acetone/ether to give 9.672 g of the product (54.2% yield).

Example 42

Reaction Procedure

Figure 22:
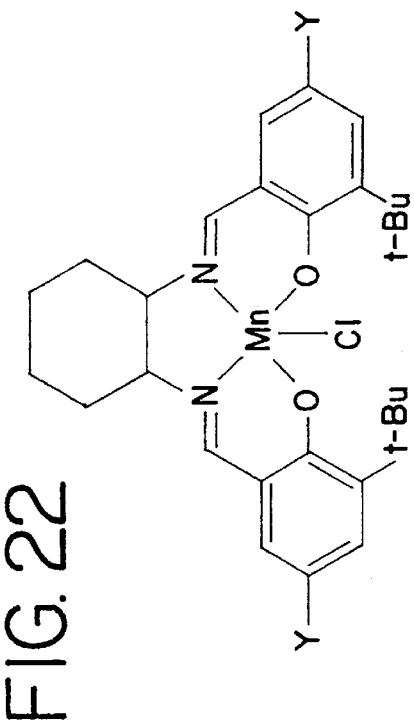
FIG. 22 shows the generalized structure of a preferred catalyst used in catalytic disproportionation of hydrogen peroxide.
Figure 23:
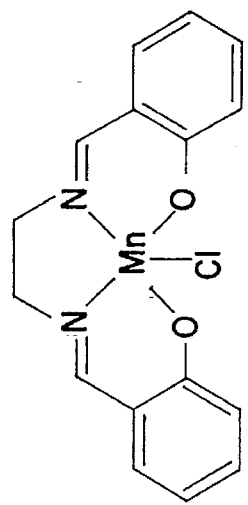
FIG. 23 shows the generalized structure of another preferred catalyst used in catalytic disproportionation of hydrogen peroxide.

A small round bottom flask equipped with a septum was charged with the catalyst (0.1 mol %) and 1 ml of the solvent. To this solution was added a buffered solution of H$_2$O$_2$. The rate and conversion of the reaction were monitored by trapping the O$_2$ evolved from the reaction. Table VII below shows the turnover values for several catalysts, whose generalized structures are shown in FIGS. 22 and 23. Turnovers are defined as moles of H$_2$O$_2$ destroyed per mole of catalyst.

TABLE VII

| Catalyst | Solvent | Turnovers |
|---|---|---|
| Mn-salen complex, 5-t-Bu, 3-t-Bu substituents | EtOH | 685 |
| Mn-salen complex, 5-t-Bu, 3-t-Bu substituents | Acetone | 316 |
| Mn-salen complex, 5-t-Bu, 3-t-Bu substituents | $CH_2Cl_2$ | 804 |
| Mn-salen complex, 5-Cl, 3-t-Bu substituents | $CH_2Cl_2$ | 608 |
| Mn-salen complex, 5-Me, 3-t-Bu substituents | $CH_2Cl_2$ | 660 |

TABLE VII-continued

| Catalyst | Solvent | Turnovers |
|---|---|---|
| [Mn salen complex with cyclohexane-diyl bridge, 5-MeO and 3-t-Bu substituents, Cl ligand] | CH$_2$Cl$_2$ | 741 |
| [Mn salen complex with ethylene bridge, Cl ligand] | CH$_2$Cl$_2$ | 145 |
| [Mn salen complex with propylene bridge, Cl ligand] | CH$_2$Cl$_2$ | 211 |
| [Mn salen complex with propylene bridge, Cl ligand] | EtOH | 67 |
| [Mn salen complex with propylene bridge, Cl ligand] | H$_2$O | 123 |
| [Mn salen complex with propylene bridge, PF$_6^-$ counterion] | H$_2$O | 153 |
| [Mn salen complex with ethylene bridge, Cl ligand] | Et$_2$O | 38 |

We claim:

1. A chiral catalyst having the following general formula:

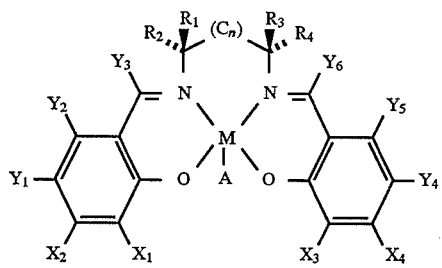

where M is a transition metal ion in the +3 oxidation state;
where A is an anion;
where n is either 0, 1, or 2;
where at least one of X1 or X2 is selected from the group consisting of aryls, primary alkyls, secondary alkyls, tertiary alkyls, and alkyl groups bearing hetero atoms;
where at least one of X3 or X4 is selected from the group consisting of aryls, primary alkyls, secondary alkyls, tertiary alkyls, and alkyl groups bearing hetero atoms;
where Y1, Y2, Y3, Y4, Y5, and Y6 are independently selected from the group consisting of hydrogen, halides, alkyls, aryls, NO$_2$, and alkyl groups bearing hetero atoms;
where at least one of R1, R2, R3 and R4 is selected from a first group consisting of hydrogen, CH$_3$, and primary alkyls;
where, if R1 is selected from said first group, then R2 and R3 are selected from a second group consisting of aryls, secondary alkyls, tertiary alkyls, and alkyls bearing hetero atoms;
where, if R2 is selected from said first group, then R1 and R4 are selected from said second group;
where, if R3 is selected from said first group, then R1 and R4 are selected from said second group; and
where, if R4 is selected from said first group, then R2 and R3 are selected from said second group.

2. The catalyst of claim 1 wherein the metal ion is Mn.
3. The catalyst of claim 1 wherein said first group consists of hydrogen and methyl.
4. The catalyst of claim 1 wherein said second group consists of t-butyl and phenyl.
5. The catalyst of claim 1 wherein R1 is the same as R4 and R2 is the same as R3.
6. The catalyst of claim 1 wherein X1 and X3 are independently selected from the group consisting of t-butyl and phenyl.
7. A chiral catalyst having the following general formula:

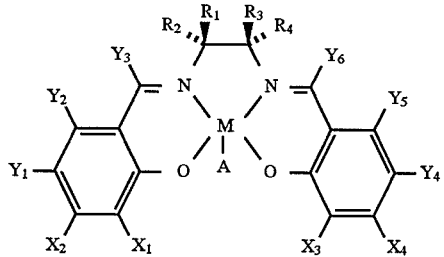

where M is a transition metal ion selected from the group consisting of Mn, Cr, Fe, Co, Ti, V, Ru, and Os;

where A is an anion;
where X1 and X3 are the same and are selected from the group consisting of aryls, primary alkyls, secondary alkyls, tertiary alkyls, and alkyl groups bearing hetero atoms;
where X2, X4, Y1, Y2, Y3, Y4, Y5, and Y6 are independently selected from the group consisting of hydrogen, halides, alkyls, aryls, NO2, and alkyl groups bearing hetero atoms;
where R1 and R4 are the same and are either selected from a first group consisting of H, CH$_3$, C$_2$H$_5$, and primary alkyls, or selected from a second group consisting of aryls, secondary alkyls, tertiary alkyls, and alkyls bearing hetero atoms;
where R2 and R3 are the same and are either selected from said second group if R1 and R4 are selected from said first group, or selected from said first group if R1 and R4 are selected from said second group.

8. The catalyst of claim 7 wherein the metal ion is Mn.
9. The catalyst of claim 7 wherein said first group consists of hydrogen.
10. The catalyst of claim 7 wherein said second group consists of t-butyl and phenyl.
11. A chiral catalyst having the following general formula:

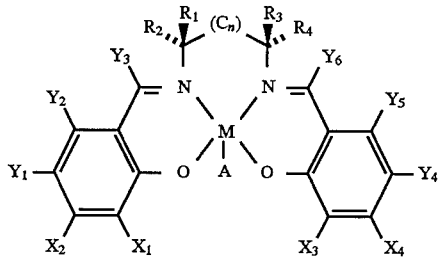

where M is a transition metal ion in the +3 oxidation state;
where A is an anion;
where n is either 0, 1, or 2;
where at least one of X1 or X2 is selected from the group consisting of aryls, primary alkyls, secondary alkyls, tertiary alkyls, and alkyl groups bearing hetero atoms;
where at least one of X3 or X4 is selected from the group consisting of aryls, primary alkyls, secondary alkyls, tertiary alkyls, and alkyl groups bearing hetero atoms;
where at least one of Y1 or Y2 is selected from the group consisting of aryls, primary alkyls, secondary alkyls, tertiary alkyls, halides, NO$_2$, and alkyl groups bearing hetero atoms;
where at least one of Y4 or Y5 is selected from the group consisting of aryls, primary alkyls, secondary alkyls, tertiary alkyls, halides, NO$_2$, and alkyl groups bearing hetero atoms;
where Y3 and Y6 are independently selected from the group consisting of H and primary alkyl groups;
where either one or two of R1, R2, R3 and R4 is hydrogen;
where, if R1 is hydrogen, then R3 is a primary alkyl;
where, if R2 is hydrogen, then R4 is a primary alkyl;
where, if R3 is hydrogen, then R1 is a primary alkyl; and
where, if R4 is hydrogen, then R2 is a primary alkyl.

12. The catalyst of claim 11 wherein the metal ion is Mn.
13. The catalyst of claim 11 wherein R1 is the same as R4 and R2 is the same as R3.

14. The catalyst of claim 11 wherein X1 and X3 are independently selected from the group consisting of t-butyl and phenyl.

15. The catalyst of claim 14 wherein Y1 and Y4 are independently selected from the group consisting of t-butyl and phenyl.

16. The catalyst of claim 14 wherein X1, X3, Y1 and Y4 are all the same.

17. The catalyst of claim 11 wherein R1 and R4 are hydrogen and R2 and R3 are methyl.

18. A chiral catalyst having the following general formula when in the active state:

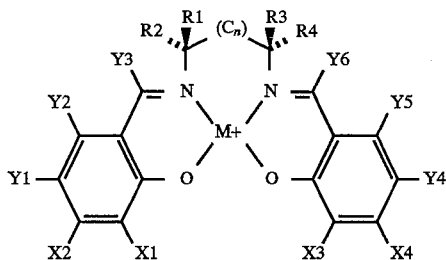

where M is a transition metal ion in the +3 oxidation state;

where n is either 0, 1, or 2;

where at least one of X1 or X2 is selected from the group consisting of aryls, primary alkyls, secondary alkyls, tertiary alkyls, and alkyl groups bearing hetero atoms;

where at least one of X3 or X4 is selected from the group consisting of aryls, primary alkyls, secondary alkyls, tertiary alkyls, and alkyl groups bearing hetero atoms;

where Y1, Y2, Y3, Y4, Y5, and Y6 are independently selected from the group consisting of hydrogen, halides, alkyls, aryls, $NO_2$, and alkyl groups bearing hetero atoms;

where at least one of R1, R2, R3 and R4 is selected from a first group consisting of hydrogen, $CH_3$, and primary alkyls;

where, if R1 is selected from said first group, then R2 and R3 are selected from a second group consisting of aryls, secondary alkyls, tertiary alkyls, and alkyls bearing hetero atoms;

where, if R2 is selected from said first group, then R1 and R4 are selected from said second group;

where, if R3 is selected from said first group, then R1 and R4 are selected from said second group; and where, if R4 is selected from said first group, then R2 and R3 are selected from said second group.

19. The catalyst of claim 18 wherein the metal ion is Mn.

20. The catalyst of claim 18 wherein said first group consists of hydrogen and methyl.

21. The catalyst of claim 18 wherein said second group consists of t-butyl and phenyl.

22. The catalyst of claim 18 wherein R1 is the same as R4 and R2 is the same as R3.

23. The catalyst of claim 18 wherein X1 and X3 are independently selected from the group consisting of t-butyl and phenyl.

24. A chiral catalyst having the following general formula when in the active state:

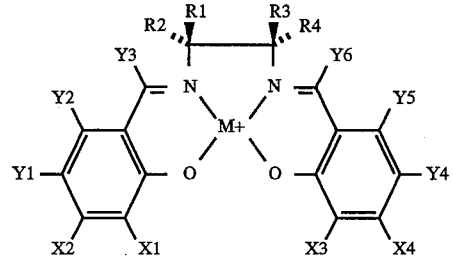

where M is a transition metal ion selected from the group consisting of Mn, Cr, Fe, Co, Ti, V, Ru, and Os;

where X1 and X3 are the same and are selected from the group consisting of aryls, primary alkyls, secondary alkyls, tertiary alkyls, and alkyl groups bearing hetero atoms;

where X2, X4, Y1, Y2, Y3, Y4, Y5, and Y6 are independently selected from the group consisting of hydrogen, halides, alkyls, aryls, $NO_2$, and alkyl groups bearing hetero atoms;

where R1 and R4 are the same and are either selected from a first group consisting of H, $CH_3$, $C_2H_5$, and primary alkyls, or selected from a second group consisting of aryls, secondary alkyls, tertiary alkyls, and alkyls bearing hetero atoms;

where R2 and R3 are the same and are either selected from said second group if R1 and R4 are selected from said first group, or selected from said first group if R1 and R4 are selected from said second group.

25. The catalyst of claim 24 wherein the metal ion is Mn.

26. The catalyst of claim 24 wherein said first group consists of hydrogen.

27. The catalyst of claim 24 wherein said second group consists of t-butyl and phenyl.

28. A chiral catalyst having the following general formula when in the active state:

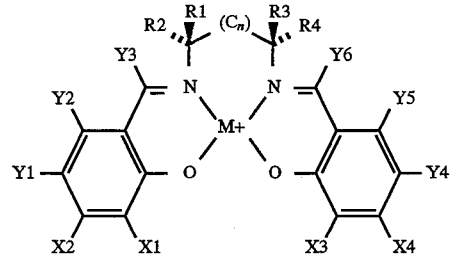

where M is a transition metal ion in the +3 oxidation state;

where n is either 0, 1, or 2;

where at least one of X1 or X2 is selected from the group consisting of aryls, primary alkyls, secondary alkyls, tertiary alkyls, and alkyl groups bearing hetero atoms;

where at least one of X3 or X4 is selected from the group consisting of aryls, primary alkyls, secondary alkyls, tertiary alkyls, and alkyl groups bearing hetero atoms;

where at least one of Y1 or Y2 is selected from the group consisting of aryls, primary alkyls, secondary alkyls, tertiary alkyls, halides, $NO_2$, and alkyl groups bearing hetero atoms;

where at least one of Y4 or Y5 is selected from the group consisting of aryls, primary alkyls, secondary alkyls, tertiary alkyls, halides, $NO_2$, and alkyl groups bearing hetero atoms;

where Y3 and Y6 are independently selected from the group consisting of H and primary alkyl groups;

where either one or two of R1, R2, R3 and R4 is hydrogen;

where, if R1 is hydrogen, then R3 is a primary alkyl;

where, if R2 is hydrogen, then R4 is a primary alkyl;

where, if R3 is hydrogen, then R1 is a primary alkyl; and where, if R4 is hydrogen, then R2 is a primary alkyl.

29. The catalyst of claim 28 wherein the metal ion is Mn.

30. The catalyst of claim 28 wherein R1 is the same as R4 and R2 is the same as R3.

31. The catalyst of claim 28 wherein X1 and X3 are independently selected from the group consisting of t-butyl and phenyl.

32. The catalyst of claim 31 wherein Y1 and Y4 are independently selected from the group consisting of t-butyl and phenyl.

33. The catalyst of claim 31 wherein X1, X3, Y1 and Y4 are all the same.

34. The catalyst of claim 28 wherein R1 and R4 are hydrogen and R2 and R3 are methyl.

35. A chiral catalyst having the following general formula:

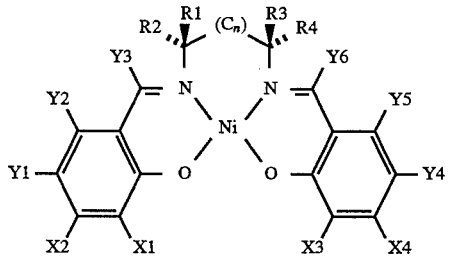

where n is either 0, 1, or 2;

where at least one of X1 or X2 is selected from the group consisting of aryls, primary alkyls, secondary alkyls, tertiary alkyls, and alkyl groups bearing hetero atoms;

where at least one of X3 or X4 is selected from the group consisting of aryls, primary alkyls, secondary alkyls, tertiary alkyls, and alkyl groups bearing hetero atoms;

where Y1, Y2, Y3, Y4, Y5, and Y6 are independently selected from the group consisting of hydrogen, halides, alkyls, aryls, NO$_2$, and alkyl groups bearing hetero atoms;

where at least one of R1, R2, R3 and R4 is selected from a first group consisting of hydrogen, CH$_3$, and primary alkyls;

where, if R1 is selected from said first group, then R2 and R3 are selected from a second group consisting of aryls, secondary alkyls, tertiary alkyls, and alkyls bearing hetero atoms;

where, if R2 is selected from said first group, then R1 and R4 are selected from said second group;

where, if R3 is selected from said first group, then R1 and R4 are selected from said second group; and where, if R4 is selected from said first group, then R2 and R3 are selected from said second group.

36. A chiral catalyst having the following general formula:

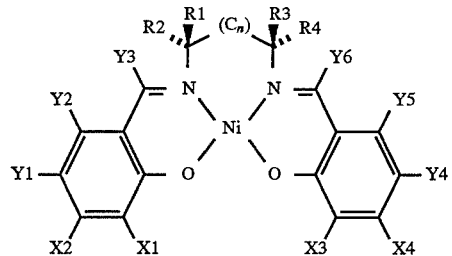

where n is either 0, 1, or 2;

where at least one of X1 or X2 is selected from the group consisting of aryls, primary alkyls, secondary alkyls, tertiary alkyls, and alkyl groups bearing hetero atoms;

where at least one of X3 or X4 is selected from the group consisting of aryls, primary alkyls, secondary alkyls, tertiary alkyls, and alkyl groups bearing hetero atoms;

where at least one of Y1 or Y2 is selected from the group consisting of aryls, primary alkyls, secondary alkyls, tertiary alkyls, halides, NO$_2$, and alkyl groups bearing hetero atoms;

whereat least one of Y4 or Y5 is selected from the group consisting of aryls, primary alkyls, secondary alkyls, tertiary alkyls, halides, NO$_2$, and alkyl groups bearing hetero atoms;

where Y3 and Y6 are independently selected from the group consisting of H and primary alkyl groups;

where either one or two of R1, R2, R3 and R4 is hydrogen;

where, if R1 is hydrogen, then R3 is a primary alkyl;

where, if R2 is hydrogen, then R4 is a primary alkyl;

where, if R3 is hydrogen, then R1 is a primary alkyl; and, where, if R4 is hydrogen, then R2 is a primary alkyl.

37. A method of enantioselectively epoxidizing a prochiral olefin with the use of a chiral catalyst comprising the steps of:

providing a prochiral olefin;

providing an oxygen atom source;

providing the chiral catalyst of claims 1, 7, 11, 18, or 28; and reacting said olefin, said oxygen atom source, and said chiral catalyst under such conditions and for such time sufficient to epoxidize said olefin.

38. The method of claim 37 wherein the prochiral olefin is selected from the group consisting of monosubstituted and cis 1,2 disubstituted olefins.

39. The method of claim 37 wherein the prochiral olefin is a cis disubstituted olefin bearing a primary substituent on one side of the double bond and a secondary, tertiary, or aryl substituent on the other side.

40. The method of claim 37 wherein the olefin is selected from the group consisting of:

cis-8-methylstyrene, dihydronaphthalene, 2-cyclohexenyl-1,1-dioxolane, 2,2-dimethylchromene, styrene, and propylene.

41. The method of claim 37 wherein the oxygen atom source is selected from the group consisting of NaOCl, iodosylmesitylene, NaIO$_4$, NBu$_4$IO$_4$, potassium peroxymonosulfate, magnesium monoperoxyphthalate, and hexacyanoferrate ion.

42. The method of claim 37 wherein, the oxygen atom source is selected from group consisting of NaOCl and iodosylmesitylene.

43. The method of claim 37 further comprising the step of adding a pyridine-N-oxide derivative to the olefin, the oxygen atom source, and the chiral catalyst.

44. The method of claim 43 wherein the pyridine-N-oxide derivative is selected from the group consisting of 4-phenylpyridine-N-oxide and 4-t-butylpyridine-N-oxide.

45. The method of claim 43 wherein the olefin is selected from the group consisting of cis-8-methylstyrene, dihydronaphthalene, 2-cyclohexenyl-1,1-dioxolane, 2,2-dimethylchromene, styrene, and propylene.

46. A method of enantioselectively epoxidizing a chromene derivative with a chiral catalyst comprising the steps of:

providing a chromene derivative having the general formula:

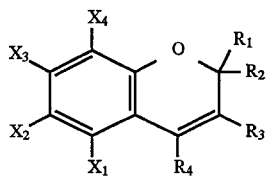

wherein R1, R2, R3, R4, X1, X2, X3 and X4 are each selected from the group consisting of hydrogen, aryls, primary alkyls, secondary alkyls, tertiary alkyls, alkyl groups bearing hetero atoms, and silyls, and wherein no more than one of R1 and R2 are hydrogen;

providing an oxygen atom source;

providing the chiral catalyst of claim 1, 7, 11, 18, or 28; and reacting said chromene derivative, said oxygen atom source, and said chiral catalyst under such conditions and for such time sufficient to epoxidize said chromene derivative, to thereby produce an epoxychroman.

47. The method of claim 46 wherein R1 and R2 on the chromene derivative are the same.

48. The method of claim 46 wherein the R1 and R2 on the chromene derivative are alkyl groups.

49. The method of claim 46 wherein R1 and R2 on the chromene derivative are methyl groups.

50. The method of claim 46 wherein the chromene derivative is 6-cyano-2,2-dimethylchromene.

51. The method of claim 46 wherein the oxygen atom source is NaOCl.

52. The method of claim 46 wherein the transition metal ion is selected from the group consisting of Mn, Cr, Fe, and Co.

53. The method of claim 46 further comprising the step of adding a pyridine-N-oxide derivative to the chromene derivative, the oxygen atom source, and the chiral catalyst.

54. The method of claim 53 wherein the pyridine-N-oxide derivative is selected from the group consisting of 4-phenylpyridine-N-oxide and 4-t-butylpyridine-N-oxide.

55. The method of claim 46 wherein the opposite enantiomer of the chiral catalyst is included to thereby produce a racemic mixture of the epoxychroman.

56. A method of enantioselectively epoxidizing a cis-cinnamate derivative with a chiral catalyst to produce a cis-epoxide of said cinnamate derivative, said method comprising the steps of:

providing a cis-cinnamate derivative having the general formula:

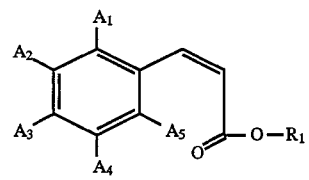

wherein A1–A5 are each selected from the group consisting of hydrogen, aryls, primary alkyls, secondary alkyls, tertiary alkyls, hydroxyl, alkoxy groups, F, Cl, Br, I, and amines;

providing an oxygen atom source;

providing the chiral catalyst defined in claims 1, 7, 11, 18, or 28; and reacting said cis-cinnamate derivative, said oxygen atom source, and said chiral catalyst under such conditions and for such time sufficient to epoxidize said cis-cinnamate derivative, to thereby produce a cis-epoxide of said cinnamate derivative.

57. The method of claim 56 further comprising the step of adding a pyridine-N-oxide derivative to the cis-cinnamate, the oxygen atom source, and the chiral catalyst.

58. The method of claim 57 wherein said pyridine-N-oxide derivative is selected from the group consisting of 4-phenylpyridine-N-oxide and 4-t-butylpyridine-N-oxide.

59. The method of claim 56 wherein the A1–A5 groups on the cis-cinnamate derivative are all the same.

60. The method of claim 56 wherein the A1–A5 groups on the cis-cinnamate derivative are hydrogen.

61. The method of claim 56 wherein R1 on the cis-cinnamate derivative is an ethyl group.

62. The method of claim 56 wherein the cis-cinnamate derivative is cis-ethyl cinnamate.

63. The method of claim 56 wherein the oxygen atom source is NaOCl.

64. The method of claim 56 wherein the transition metal ion is manganese.

65. A method of making a C-13 side chain of taxol or taxol derivative, said method comprising the steps of:

providing a cis-cinnamate derivative having the general formula:

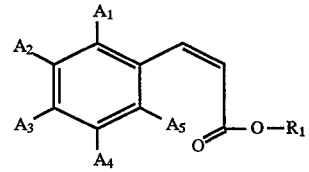

wherein A1–A5 are each selected from the group consisting of hydrogen, aryls, primary alkyls, secondary, alkyls, tertiary alkyls, hydroxyl, alkoxy, F, Cl, Br, I, and; amines;

wherein said alkoxy is selected from the group consisting of alkyls, aryls, aroyls, or alkanoyls;

wherein R1 is an alkyl group;

providing an oxygen atom source;

providing the chiral catalyst defined in claims 1, 7, 11, 18, or 28;

reacting said cis-cinnamate derivative, said oxygen atom source, and said chiral catalyst under such conditions and for such time sufficient to epoxidize said cis-cinnamate derivative, to thereby produce a cis-epoxide of said cinnamate derivative;

regioselectively opening said cis-epoxide of cinnamate derivative to produce a 3-phenyl-isoserinamide derivative;

hydrolyzing said 3-phenyl-isoserinamide derivative to produce a 3-phenyl-isoserine derivative;

providing benzoyl chloride in sodium bicarbonate solution; and reacting said 3-phenyl-isoserine derivative with said benzoyl chloride in sodium bicarbonate to form N-benzoyl-3-phenyl-isoserine.

66. The method of claim 65 further comprising the step of adding a pyridine-N-oxide derivative to the cis-cinnamate derivative, the oxygen atom source, and the chiral catalyst.

67. The method of claim 66 wherein said pyridine-N-oxide is selected from the group consisting of 4-phenylpyridine-N-oxide and 4-t-butyl-pyridine-N-oxide.

68. The method of claim 65 wherein the A1–A5 groups on the cis-cinnamate derivative are the same.

69. The method of claim 65 wherein the A1–A5 groups on the cis-cinnamate derivative are hydrogen.

70. The method of claim 65 wherein R1 on the cis-cinnamate derivative is an ethyl group.

71. The method of claim 65 wherein the cis-cinnamate derivative is cis-ethyl cinnamate.

72. The method of claim 65 wherein the oxygen atom source is NaOCl.

73. The method of claim 65 wherein the transition metal ion is Mn.

74. A method of producing taxol, said method comprising the steps of:

providing an ethyl phenylpropiolate;

partially hydrogenating ethyl phenylpropiolate to produce cis-ethyl cinnamate;

providing an oxygen atom source;

providing the chiral catalyst defined in claims 1, 7, 11, 18, or 28;

reacting said cis-ethyl cinnamate, said oxygen atom source, and said chiral catalyst under such conditions and for such time sufficient to epoxidize said cis-ethyl cinnamate, to thereby produce a cis-epoxide of ethyl cinnamate;

regioselectively opening said cis-epoxide of ethyl cinnamate to produce 3-phenyl-isoserinamide;

hydrolyzing said 3-phenyl-isoserinamide to produce 3-phenyl-isoserine;

providing benzoyl chloride in sodium bicarbonate solution;

reacting said 3-phenyl-isoserine with said benzoyl chloride in sodium bicarbonate to form N-benzoyl-3-phenyl-isoserine;

reacting said N-benzoyl-3-phenyl-isoserine with 1-chloroethyl ethyl ether and tertiary amine in methylene chloride to form-N-benzoyl-O-(1-ethoxyethyl)-3-phenyl-isoserine for the C13 side chain;

providing an alcohol with the general formula:

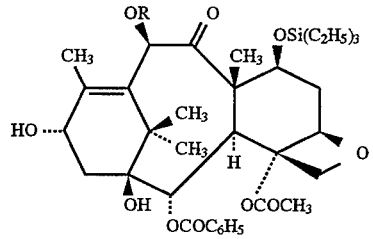

wherein R is a hydroxyl protecting group;

reacting, in the presence of a tertiary amine activating agent, said N-benzoyl-O-(1-ethoxyethyl)-3-phenyl-isoserine and said alcohol to form an intermediate; and converting the intermediate to taxol by hydrolyzing the ethoxyethyl on the C13 side chain and the R hydroxyl protecting groups.

75. The method of claim 74 R is selected from ethers, esters, carbonates and silyl groups.

76. The method of claim 74 wherein R is selected from ethoxyethyl, trimethyl, allyl or triethyl silyl.

77. The method of claim 74 wherein the tertiary amine activating agent is triethyl amine, diisopropyl ethyl amine, pyridine, N-methyl imidazole, or 4-dimethylaminopyridine.

78. The method of claim 74 further comprising the steps of adding a pyridine-N-oxide derivative to the cis-cinnamate derivative, the oxygen atom source, and the chiral catalyst.

79. The method of claim 78 wherein said pyridine-N-oxide derivative is selected from the group consisting of 4-phenylpyridine-N-oxide and 4-t-butylpyridine-N-oxide.

80. The method of claim 74 wherein the transition metal ion is Mn.

81. A chiral catalyst having the following formula:

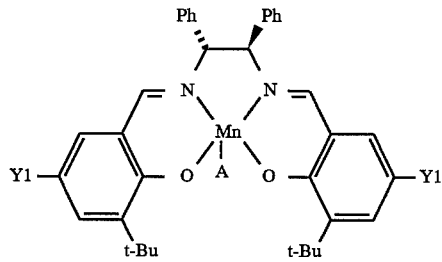

wherein Y is selected from the group consisting of O—CH$_3$, t-butyl and methyl; and wherein A in an anion.

* * * * *